US011324912B2

(12) United States Patent
Acker et al.

(10) Patent No.: US 11,324,912 B2
(45) Date of Patent: May 10, 2022

(54) SYSTEMS AND METHODS FOR INDICATING LIFETIME OF AN $NO_2$-TO-NO REACTOR CARTRIDGE USED TO DELIVER NO FOR INHALATION THERAPY TO A PATIENT

(71) Applicant: Mallinckrodt Pharmaceuticals Ireland Limited, Dublin (IE)

(72) Inventors: Jaron Acker, Madison, WI (US); Muhammad Asif, New Fairfield, CT (US); Craig Flanagan, Belmar, NJ (US); Douglas Alan Greene, Basking Ridge, NJ (US); Sarah Jayne Ridley, Philipsburg, NJ (US); Frank Kenneth Schweighardt, Allentown, PA (US); Lien-Lung Sheu, Berkeley Heights, NJ (US)

(73) Assignee: Mallinckrodt Pharmaceuticals Ireland Limited, Dub (IE)

( * ) Notice: Subject to any disclaimer, the term of this patent is extended or adjusted under 35 U.S.C. 154(b) by 338 days.

(21) Appl. No.: 16/696,142

(22) Filed: Nov. 26, 2019

(65) Prior Publication Data
US 2020/0094010 A1    Mar. 26, 2020

Related U.S. Application Data

(63) Continuation of application No. 14/712,419, filed on May 14, 2015, now Pat. No. 10,525,226.

(Continued)

(51) Int. Cl.
*A61M 16/12* (2006.01)
*C01B 21/24* (2006.01)
(Continued)

(52) U.S. Cl.
CPC ........ *A61M 16/12* (2013.01); *A61M 16/0051* (2013.01); *A61M 16/024* (2017.08);
(Continued)

(58) Field of Classification Search
CPC .......... A61M 2205/707; A61M 16/202; A61M 2205/3306; A61M 2205/584;
(Continued)

(56) References Cited

U.S. PATENT DOCUMENTS

| 5,827,420 | A | * | 10/1998 | Shirazi | ...................... | C25B 9/19 205/220 |
| 6,158,434 | A | * | 12/2000 | Lugtigheid | ........... | A61M 16/12 128/204.22 |

(Continued)

*Primary Examiner* — Tu A Vo

(57) ABSTRACT

The principles and embodiments of the present invention relate to methods and systems for safely providing NO to a recipient for inhalation therapy. There are many potential safety issues that may arise from using a reactor cartridge that converts $NO_2$ to NO, including exhaustion of consumable reactants of the cartridge reactor. Accordingly, various embodiments of the present invention provide systems and methods of determining the remaining useful life of a NO2-to-NO reactor cartridge and/or a break-through of $NO_2$, and providing an indication of the remaining useful life and/or break-through.

17 Claims, 12 Drawing Sheets

Related U.S. Application Data

(60) Provisional application No. 61/996,798, filed on May 14, 2014.

(51) Int. Cl.
| | | |
|---|---|---|
| *B01D 53/04* | (2006.01) | |
| *A61M 16/06* | (2006.01) | |
| *A61M 16/00* | (2006.01) | |
| *A61M 16/10* | (2006.01) | |
| *A61M 16/16* | (2006.01) | |
| *A61M 16/20* | (2006.01) | |

(52) U.S. Cl.
CPC ............ *A61M 16/06* (2013.01); *A61M 16/10* (2013.01); *B01D 53/0415* (2013.01); *C01B 21/24* (2013.01); *A61M 16/0063* (2014.02); *A61M 16/16* (2013.01); *A61M 16/161* (2014.02); *A61M 16/202* (2014.02); *A61M 2016/003* (2013.01); *A61M 2016/1035* (2013.01); *A61M 2202/0275* (2013.01); *A61M 2205/12* (2013.01); *A61M 2205/18* (2013.01); *A61M 2205/3306* (2013.01); *A61M 2205/3317* (2013.01); *A61M 2205/3324* (2013.01); *A61M 2205/3368* (2013.01); *A61M 2205/3569* (2013.01); *A61M 2205/3592* (2013.01); *A61M 2205/50* (2013.01); *A61M 2205/581* (2013.01); *A61M 2205/583* (2013.01); *A61M 2205/584* (2013.01); *A61M 2205/707* (2013.01); *B01D 53/0446* (2013.01); *B01D 2253/106* (2013.01); *B01D 2257/404* (2013.01); *B01D 2259/4533* (2013.01)

(58) Field of Classification Search
CPC ...... A61M 2205/583; A61M 2205/581; A61M 2205/3592; A61M 2205/3569; A61M 2205/3368; A61M 2205/3324; A61M 16/161; A61M 2205/12; A61M 2016/1035; A61M 2205/3546; A61M 2205/70; A61M 2205/3334; A61M 2205/50; A61M 2016/003; A61M 2202/0275; A61M 2205/18; A61M 16/12; A61M 16/024; A61M 16/0051; A61M 16/06; A61M 16/10; A61M 16/0063; A61M 16/16; A61M 2205/3317; B01D 53/0415; B01D 53/0446; B01D 2253/106; B01D 2257/404; B01D 2259/4533; C01B 21/24

See application file for complete search history.

(56) References Cited

U.S. PATENT DOCUMENTS

| | | | | |
|---|---|---|---|---|
| 6,962,154 | B2* | 11/2005 | Krebs | A61M 16/009 128/202.22 |
| 7,947,227 | B2* | 5/2011 | Fine | A61P 11/00 422/120 |
| 7,955,294 | B2* | 6/2011 | Stenzler | A61M 16/122 604/23 |
| 8,173,072 | B2* | 5/2012 | Fine | C01B 21/24 422/129 |
| 8,652,064 | B2* | 2/2014 | Wood, Jr. | A61B 5/097 600/532 |
| 2006/0180147 | A1* | 8/2006 | Rounbehler | C01B 21/24 128/203.12 |
| 2006/0207594 | A1* | 9/2006 | Stenzler | A61M 16/204 128/204.18 |
| 2007/0062527 | A1* | 3/2007 | Montgomery | A61M 16/04 128/204.21 |
| 2007/0190184 | A1* | 8/2007 | Montgomery | A61M 16/0003 424/718 |
| 2007/0243113 | A1* | 10/2007 | DiLeo | B01D 29/60 422/119 |
| 2009/0241947 | A1* | 10/2009 | Bedini | A61M 16/0666 128/203.14 |
| 2009/0314289 | A1* | 12/2009 | Fine | C01B 21/32 128/203.12 |
| 2010/0018526 | A1* | 1/2010 | Miller | A61M 16/10 128/203.12 |
| 2010/0043788 | A1* | 2/2010 | Fine | A61P 1/08 128/202.26 |
| 2010/0043789 | A1* | 2/2010 | Fine | A61M 16/10 128/203.12 |
| 2010/0051025 | A1* | 3/2010 | Zapol | A61P 9/10 128/203.12 |
| 2011/0220103 | A1* | 9/2011 | Fine | A61M 16/104 128/202.26 |
| 2011/0240019 | A1* | 10/2011 | Fine | A61M 16/12 128/202.26 |
| 2012/0093948 | A1* | 4/2012 | Fine | A61M 16/10 424/718 |
| 2012/0240927 | A1* | 9/2012 | Bathe | A61M 16/024 128/203.12 |
| 2013/0022691 | A1* | 1/2013 | Miller | A61L 2/0005 424/718 |
| 2013/0037023 | A1* | 2/2013 | Rounbehler | A61M 16/122 128/203.12 |
| 2013/0081626 | A1* | 4/2013 | Pujol | A61M 16/1075 128/204.17 |
| 2013/0192595 | A1* | 8/2013 | Tolmie | A61M 16/0051 128/202.22 |
| 2014/0127081 | A1* | 5/2014 | Fine | A61M 16/12 422/119 |
| 2014/0216452 | A1* | 8/2014 | Miller | A61M 16/125 128/202.26 |
| 2015/0328430 | A1* | 11/2015 | Miller | A61K 33/00 424/718 |

\* cited by examiner

SYSTEMS AND METHODS FOR INDICATING LIFETIME OF AN NO$_2$-TO-NO REACTOR CARTRIDGE USED TO DELIVER NO FOR INHALATION THERAPY TO A PATIENT

CROSS-REFERENCE TO RELATED APPLICATIONS

This application is a continuation of U.S. application Ser. No. 14/712,419, filed May 14, 2015 which claims the benefit under 35 U.S.C. § 119(e) to U.S. Provisional Application No. 61/996,798, filed May 14, 2014, the entire contents of which are incorporated herein by reference in their entirety.

TECHNICAL FIELD

Principles and embodiments of the present invention relate generally to systems and methods for determining, and/or indicating to users, the proper operation and remaining life of an NO$_2$-to-NO reactor cartridge for delivering NO to a patient, in need thereof, for inhalation therapy.

BACKGROUND

A number of gases have been shown to have pharmaceutical action in humans and animals. One such gas is Nitric Oxide (NO) that, when inhaled, acts to dilate blood vessels in the lungs, improving oxygenation of the blood and reducing pulmonary hypertension. In the field of inhalation therapy for various pulmonary conditions such as acute pulmonary vasoconstriction, hypertension and thromboembolism, or inhalation injury, treatment has included the use of the therapeutic gas NO supplied from a gas cylinder. More specifically, this gaseous NO for inhalation therapy is supplied to a patient from a high pressure gas cylinder containing NO. For example, such an approach is disclosed in U.S. Pat. No. 5,558,083 entitled "Nitric Oxide Delivery System", which is incorporated herein by reference in its entirety.

Unlike supplying NO for inhalation therapy from a high pressure NO cylinder; some have proposed supplying NO for inhalation therapy from a source of Nitrogen Dioxide (NO$_2$), which is toxic, and converting this toxic NO$_2$ into NO using a "cartridge" or "reactor" (NO$_2$-to-NO reactor cartridge) at the patient's bedside. For example, such an approach is disclosed in U.S. Pat. No. 7,560,076 ("the '076 patent") issued Jul. 14, 2009 to Rounbehler et al., and assigned to GENO, LLC, which is incorporated herein by reference in its entirety. The NO$_2$-to-NO reactor cartridge in the '076 patent is filled with a loosely packed powder of a surface-active material (e.g., silica) coated with an aqueous solution of an antioxidant (e.g., aqueous ascorbic acid). Purportedly, the reactor receives NO$_2$ that passes through the loosely packed silica coated with the aqueous ascorbic acid and undergoes a chemical reaction that converts NO$_2$ to NO, which in turn exits the reactor cartridge and is then delivered to the patient.

Substantial patient safety and efficacy concerns arise from converting toxic NO$_2$ to NO at the patient's bedside as proposed because of at least the toxic nature of NO$_2$. For example, as pointed out in the '076 patent, "unlike NO, the part per million levels of NO$_2$ gas is highly toxic if inhaled and can form nitric and nitrous acid in the lungs."

Compounding risks relating to such NO$_2$ to NO conversion at the patient's bedside, the ability of these NO$_2$-to-NO reactor cartridges to convert NO$_2$ to NO exhausts as it uses a consumable reactant and this exhaustion results in the breakthrough of toxic NO$_2$, which in turn may be delivered to the patient. Without an indicator (e.g., dosage meter) to the user of the amount of lifetime remaining for the reactor as it exhausts, a user has no way of confirming how much or little lifetime the reactor has prior to at least breakthrough of toxic NO$_2$. This can force the user to guess how much lifetime the reactor has prior to at least breakthrough of toxic NO$_2$; However, factors impacting the lifetime of the reactor and/or breakthrough of toxic NO$_2$ may not be readily attainable by user observation.

Further compounding risks relating to such NO$_2$-to-NO reactor cartridges, the ability of these reactors to convert NO$_2$ to NO (e.g., lifetime) can become compromised resulting in breakthrough of toxic NO$_2$ being delivered to the patient. For example, the reactor can be compromised by a channel that allows NO$_2$ flow through the reactor cartridge without conversion to NO as disclosed in U.S. Pat. No. 8,646,445 ("the '445 patent") issued Feb. 11, 2014, to Fine et al., and assigned to GENO, LLC, which is incorporated herein by reference in its entirety. As pointed out in the '445 patent, "Creation of a channel negates the effect of the powder and renders the cartridge useless. This problem is so severe that a packed tube like this can only be used if the cartridge is vertical."

Another NO$_2$-to-NO reactor cartridge is discussed in U.S. Pat. No. 8,607,785 ("the '785 patent") issued Dec. 17, 2013, to Fine et al., and assigned to GENO, LLC, which is incorporated herein by reference in its entirety. Rather than a loosely packed reactor cartridge, the '785 patent discloses a porous solid structure, which provides a rigid structure coated with an aqueous solution of an antioxidant. However, such a porous solid structure can be brittle and have its structural integrity compromised by sudden shocks or rough handling, as might occur in a clinical setting and/or by user error, handling of the conversion reactor, and environmental factors, to name a few. For example, cracks can be formed in the structure which can provide a channel allowing flow of NO$_2$ through the reactor without conversion to NO, which in turn may be delivered to the patient. Further, cracks in the structure may not be obvious until a gas flow is applied and/or NO$_2$ breakthrough occurs. In another scenario, a crack in the porous solid structure may not initially propagate all the way through the structure until sometime later under routine usage, when a toxic NO$_2$ suddenly exits the reactor cartridge, which in turn may be delivered to the patient. Accordingly, such compromised reactors may have unforeseen shortened lifetimes.

The above are only a few of the exemplary scenarios which can result in a patient receiving toxic NO$_2$ using the proposed techniques of converting toxic NO$_2$ to NO at the patient's bedside using an exhaustible reactor cartridge when lifetime of reactor is unknown to the user. Given the risk of serious injury or death associated with inhalation of NO$_2$ along with compounding factors and/or failure modes which may not be readily attainable by a user (e.g., reactor exhaustion, channeling, compromised reactors, NO$_2$ breakthrough, etc.) a need exists to provide an indicator (e.g., dosage meter) to the user of the amount of lifetime remaining for the reactor.

SUMMARY

There are several ways to address the above problems, including monitoring the use of the reactor(s), including indicators that visually warn a user of hazardous operating conditions, detectors that detect the presence or absence of the chemical species of interest, and meters that follow the depletion and/or operation of the system in real time.

Principles and embodiment of the present invention relate to systems and methods of determining the remaining useful life of a $NO_2$-to-NO reactor cartridge and/or a break-through of $NO_2$ at concentrations that may seriously impact a patient's health.

Principles and embodiments of the present invention also relate to means of monitoring the performance of an inhalation therapy system that converts $NO_2$ to NO comprising a source of $NO_2$, a conversion reactor, and a delivery member.

Principles and embodiments of the present invention also relate to systems and methods of determining a significant and/or catastrophic break-through of $NO_2$ and preventing harmful or lethal doses of $NO_2$ from reaching the inhalation therapy recipient.

Principles and embodiments of the present invention also relate to a reactor meter that informs a user of the amount of remaining life of a reactor and provides a safety check for proper reactor operation.

Principles and embodiments of the present invention also relate to a system for safely delivering a supply of NO to a recipient, comprising a gas source that supplies a gas, wherein the gas is $NO_2$ or NO, a gas conduit connected to and in fluid communication with the gas source, a $NO_2$-to-NO reactor cartridge connected to and in fluid communication with the gas conduit, so as to allow gas to flow from the gas source to an inlet end of the conversion reactor, a means of monitoring the functioning of the conversion reactor operatively associated with the conversion reactor, a delivery conduit connected to and in fluid communication with an outlet end of the conversion reactor that allows NO gas from the conversion reactor to flow to a recipient, a computer in electronic communication with the monitoring means over a communication path, wherein the computer is configured to receive electronic signals from the monitoring means and calculate a performance value for comparison with a predetermined threshold value, and configured to generate an actuating signal when the performance value falls below the threshold value, a regulating means in electronic communication with the computer over a communication path, wherein the regulating means is configured to receive an actuating signal from the computer, and wherein the regulating means halts the delivery of the gas to a recipient.

In addition, embodiments of the present invention relate to a system which further comprises a flow meter for measuring the amount of gas entering the $NO_2$-to-NO reactor cartridge, a flow meter for measuring the amount of gas being delivered to the recipient, an $NO_2$ sensor operationally associated with the delivery conduit to determine the presence of an unacceptable level of $NO_2$ in the gas being directed to the recipient.

Principles and embodiments of the present invention also relate to a method of monitoring the performance of an $NO_2$-to-NO reactor cartridge, comprising, providing an $NO_2$-to-NO reactor cartridge comprising a conversion media, incorporating one or more sensor probes into the reactor cartridge, wherein the one or more sensor probes are operatively associated with conversion media, providing a computer in electronic communication with the meter, providing at least one meter operatively associated with at least one sensor probe, and in electrical communication with the computer, detecting physical and/or chemical characteristics of the conversion media with the sensor probe(s), measuring the detected physical and/or chemical characteristics with the operatively associated meter, communicating the measured physical and/or chemical characteristics to the computer; monitoring the communicated characteristics with the computer; and displaying the measured characteristic(s) and/or activating and alarm.

BRIEF DESCRIPTION OF THE DRAWINGS

Further features of embodiment of the present invention, their nature and various advantages will become more apparent upon consideration of the following detailed description, taken in conjunction with the accompanying drawings, which are also illustrative of the best mode contemplated by the applicants, and in which like reference characters refer to like parts throughout, where.

DETAILED DESCRIPTION

The principles and embodiments of the present invention relate to methods and systems for safely providing NO to a recipient for inhalation therapy. As described above, there are many potential safety issues that may arise from using a reactor cartridge that converts $NO_2$ to NO, including exhaustion of consumable reactants of the cartridge reactor. Accordingly, various embodiments of the present invention provide systems and methods of determining the remaining useful life of a $NO_2$-to-NO reactor cartridge and/or a break-through of $NO_2$, and providing an indication of the remaining useful life and/or break-through.

In embodiments of the present invention, the chemical and physical characteristics of the cartridge reactor and consumable reactants can be measured by suitable techniques including but not limited to volumetric and mass flow rates through the cartridge, spectroscopic analysis of consumable reactants, inert products, and/or gases, sampling and chromatography of gases, wet chemical analysis and/or quantitative detection of consumable reactants and/or gases, electrochemical analysis by voltammetry and/or amperometry, and/or quantitative detection of consumable reactants by color change.

In embodiments, meters can detect and/or measure various characteristics of the conversion reactor and/or gas streams, including but not limited to the concentration of ascorbic acid, the concentration of dehydroascorbic acid, the concentration of water ($H_2O$), the concentration of $NO_2$, the concentration of NO, the concentration of $O_2$, the concentration of $HNO_3$, the pH of at least a portion of the conversion reactor, the redox potentials of chemical species in the conversion reactor, the mass flow rate of gases, the conductance at the surface of the silica gel, and the humidity of incoming and outgoing gases.

Various embodiments of the present invention can be used, modified, and/or be affiliated with various systems for delivering a pharmaceutical gas to a patient receiving inhalation therapy. These systems can include, but are not limited to, ventilators, CPAP/Bi PAP and APAP systems, pulsed delivery systems, breathing circuits, nasal cannulas, breathing masks, and/or any other system for delivering a pharmaceutical gas to a patient receiving inhalation therapy.

Generally speaking, to provide NO inhalation therapy to patient in need thereof, these systems can include, but are not limited to, a source of gas that can provide NO as a final product, a source of air flow, a source of oxygen, a conduit that contains and/or communicates the gas and air flow to a $NO_2$-to-NO reactor cartridge, a delivery conduit that contains and communicates the NO gas and air mixture from the conversion reactor to a recipient interface.

Figure 1A:
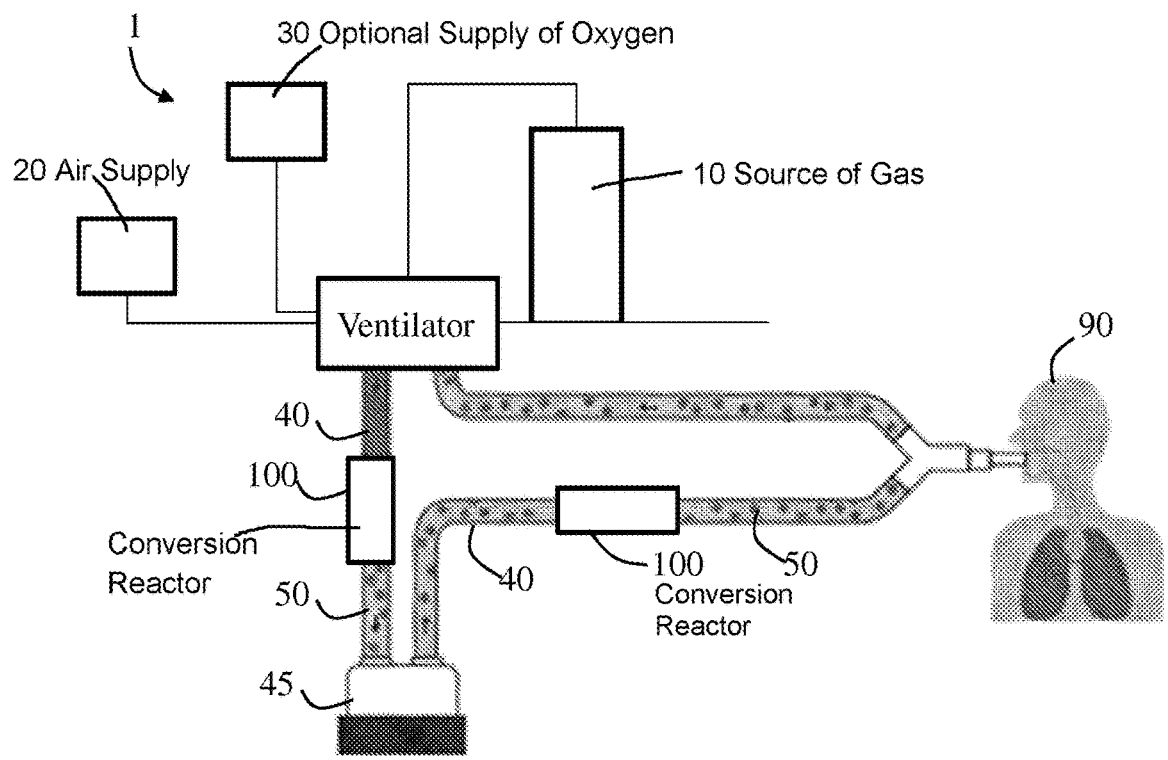
FIGS. 1A-1B illustrates exemplary inhalation therapy systems, in accordance with exemplary embodiments of the present invention.
Figure 1B:
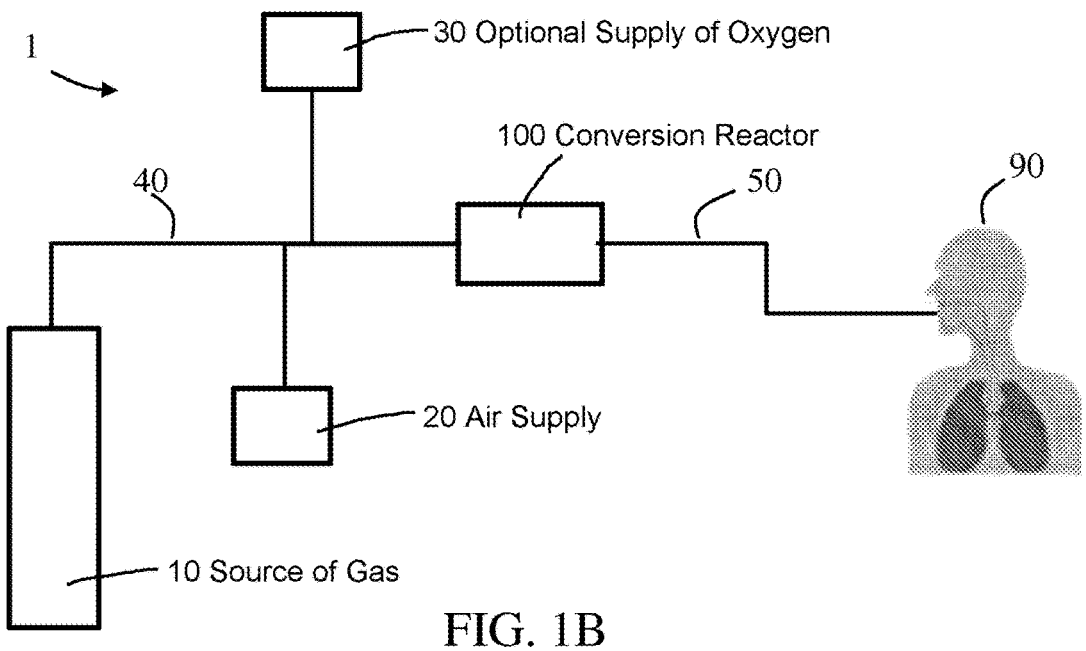

Referring to FIGS. 1A-1B, exemplary NO delivery systems are illustrated. As shown, system 1 includes a source of gas 10, which may be a $NO_2$ gas source that can be connected to and in fluid communication with gas source conduit 40 that can contain and direct the gas from the source to a conversion reactor 100 and/or humidifier 45. An air supply 20, which may be an air pump, compressor, or wall air, may be connected to and in fluid communication with the gas source conduit 40 to provide a flow of ambient air with the $NO_2$ source gas. An optional supply of oxygen 30 may also be connected to and in fluid communication with the source conduit 40, for example, to supplement the amount of oxygen being fed through the conduit(s). The source conduit 40 can be connected to and in fluid communication with the conversion reactor 100, which in turn can be connected to and in fluid communication with a gas delivery conduit 50 that contains and directs the gas from the conversion reactor to a patient 90. In embodiments, an NO gas source (not shown) may be connected to and in fluid communication with the source conduit 40, alone or in combination with the $NO_2$2 gas source.

Principles and embodiments of the present invention also relate to providing protective elements operatively associated with a source of $NO_2$, and/or a reactor cartridge, which may include components to absorb any $NO_2$ that may leak out of the $NO_2$ source and/or reactor cartridge, and color agents that indicate the presence of $NO_2$. In embodiments of the invention, the $NO_2$ may be absorbed by absorbents, including silica gel, alumina, soda lime, and magnesium sulfate. In embodiments of the invention, the presence of $NO_2$ may be indicated by sulfanilic acid (diazotizing agent) in combination with N(1-naphthyl)ethylene diamine dihydrochloride, metalloporphyrins, for example (5,10,15,20-tetraphenylporphyrin)-zinc, ethyl violet, and malachite green.

In various embodiments, a source of $NO_2$ gas may be encased within an outer housing that surrounds the container holding the $NO_2$ source material (e.g., $NO_2$ gas, $N_2O_4$ liquid, and NO gas which may react to produce $NO._2$). The $NO_2$ container and/or outer housing may be glass, quartz, silica, steel, stainless steel, chemically resistant alloys (Waspaloy®), fluoro-polymers (e.g., Teflon®), and combinations thereof (e.g., glass or fluoro-polymer lined stainless steel). In embodiments of the invention, the outer housing can be large enough to encapsulate the $NO_2$ source container or a reactor cartridge to reduce or prevent any $NO_2$ gas from reaching the atmosphere, and form an internal volume between the inside of the outer housing and the $NO_2$ source container sufficiently large to hold enough absorbent to react with all of the possibly released from the $NO_2$ source container. Reaction between the $NO_2$ gas and absorbent should be complete, such that none of the $NO_2$ remains after interacting with the absorbent. A surplus of absorbent may be included to provide a safety factor to ensure all of the $NO_2$ is absorbed and/or reacted.

In embodiments of the present invention, the absorbents may be treated and/or intermixed with the color agents, so that a color change of the color agent occurs when the absorbent interacts with the $NO_2$ or when at least a portion of the absorbent is used up. In embodiments, the color agent may be sulfanilic acid (diazotizing agent) in combination with N(1-naphthyl)ethylene diamine dihydrochloride, metalloporphyrins, for example (5,10,15,20-tetraphenylporphyrin)-zinc, ethyl violet, and malachite green. In a non-limiting example, in the absence of $NO_2$ sulfanilic acid (diazotizing agent) in combination with N(1-naphthyl)ethylene diamine dihydrochloride has white color but yields light purple color at about 3.7 ppm and medium purple at about 10 ppm of $NO_2$. In a non-limiting example, metalloporphyrins may change from purple to yellow. In embodiments, the color agent may also indicate changes in pH that occurs upon exposure to $NO_2$.

In embodiments, the outer housing may be transparent (e.g., glass, quartz, fused quartz) or have an opening in the non-transparent material body (e.g., steel) with a transparent window (e.g., glass, quartz, fused quartz), so that a user may observe any color change by the color change agent.

In embodiments of the invention, the $NO_2$-to-NO reactor cartridge, also referred to as a conversion reactor or conversion cartridge, can include an outer reactor shell or body, an inlet, an outlet, and a consumable conversion media including solid packing material coated with consumable reactant, for example an antioxidant and water, where the solid packing material can be retained within the internal volume of the reactor shell, and where the coated packing material provides a consumable reactant surface. The solid packing material and consumable reactant coating form a consumable conversion media. In one or more embodiments, the antioxidant is ascorbic acid, which can be applied to the packing material in an aqueous solution, and the packing material may be silica gel. Other antioxidants include suitable reducing agents for the conversion of $NO_2$ to NO, such as alpha tocopherol and gamma tocopherol. Other packing material may include calcium sulfate dehydrate, calcium fluorophosphate dihydrate, zirconium (IV) oxide, zircon, titanium dioxide, and aluminum silicate, or any suitable material that can be coated with consumable reactant and/or that can be hydrated.

In embodiments of the present invention, the agents for the conversion of $NO_2$ to NO also may be toluidine, benzidine, and benzidine derivatives, as presented in U.S. Pat. No. 3,106,458 issued on Oct. 8, 1963, to Grosskopf et al., and incorporated herein by reference in its entirety. The benzidine may be for example N,N,N,N'-tetraphenylbenzidine, N,N'-dimethyl-N,N' diphenylbenzidine, or N,N' diphenylbenzidine, which may be combined with a strong acid on a carrier, such as silica gel, as a reagent for $NO_2$. The toluidine, benzidine, and benzidine derivatives may be deposited onto the carrier and exposed to $NO_2$, and the toluidine, benzidine, and benzidine derivatives undergo a color change upon such exposure. In embodiments the reaction between $NO_2$ and the aromatic amines produces NO and a reactant product. For example, the N,N' diphenylbenzidine can react with $NO_2$ to produce NO, $H_2O$, and NN-diphenyl-1,4-phenylenediamine.

Figure 2A:
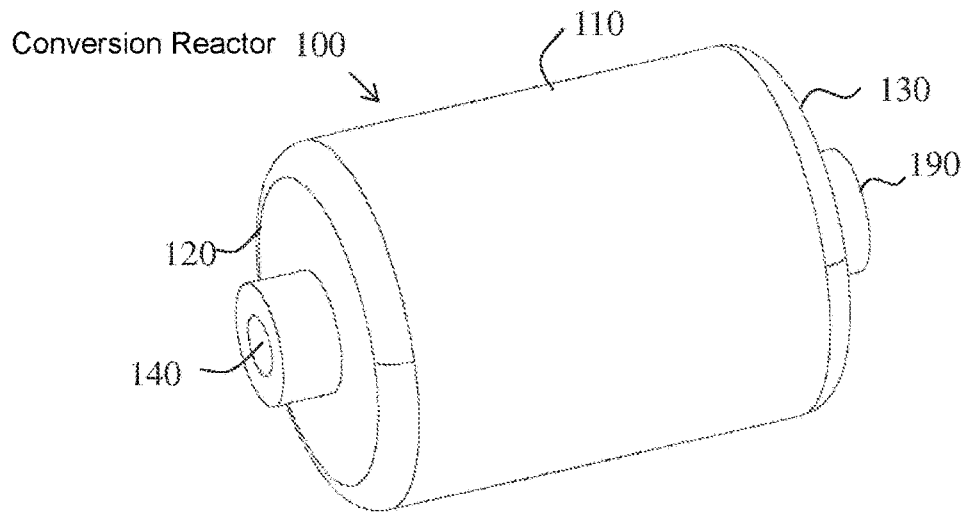
FIGS. 2A-2C illustrate an exemplary $NO_2$—NO conversion reactor, in accordance with exemplary embodiments of the present invention.
Figure 2B:
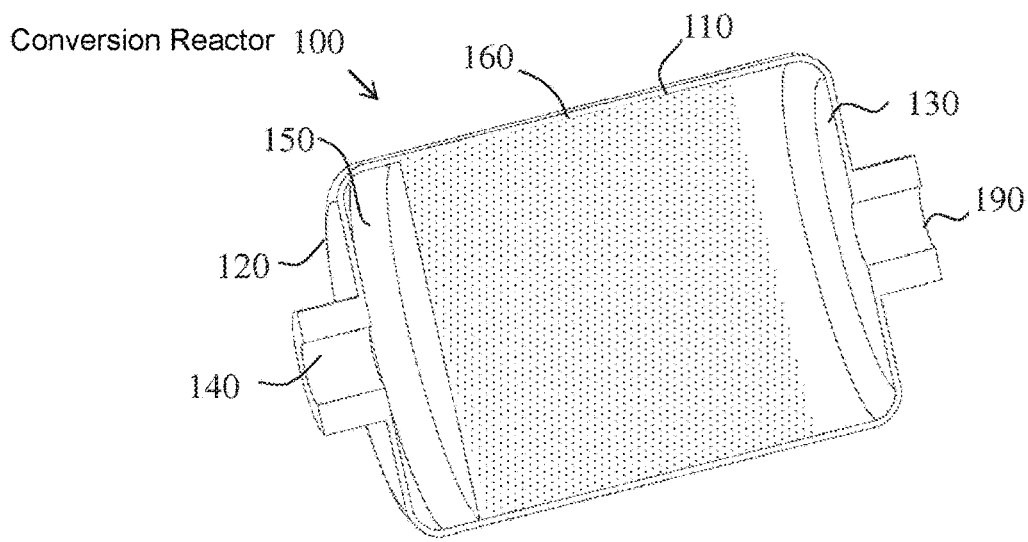
Figure 2C:
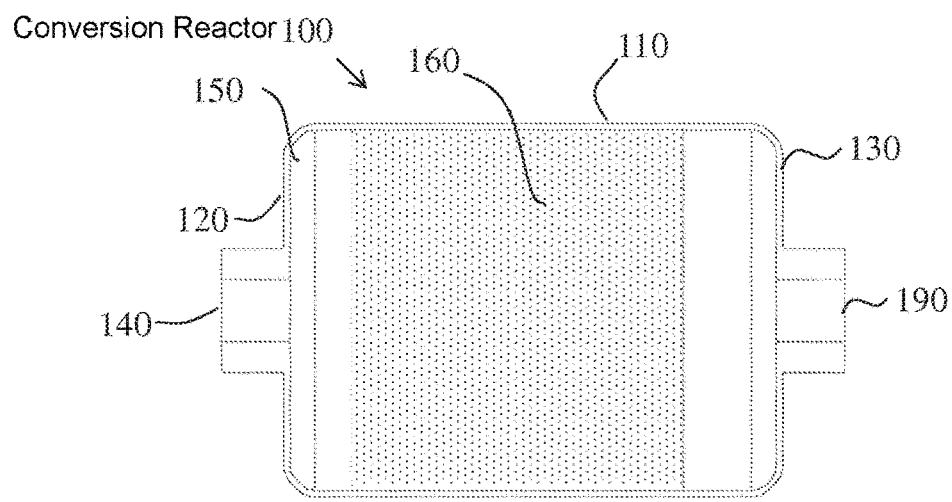

Referring to FIGS. 2A-2C, a general example of a packed-type $NO_2$-to-NO reactor cartridge 100 is illustrated. The conversion reactor has a body with an annular wall 110, an inlet end wall 120 that seals the inlet end of the reactor, and an outlet end wall 130 that seals the outlet end of the reactor to form an internal volume 150 within the reactor 100. The reactor also has an inlet 140 that facilitates connection of the reactor 100 to a gas conduit (not shown) and allows passage of gas through the inlet end wall 120 to the internal volume 150. An outlet 190 facilitates connection of the reactor 100 to another gas conduit (not shown) and allows passage of gas through the outlet end wall 130 to be delivered to a recipient. At least a portion of the internal volume 150 of the reactor 100 may contain a consumable conversion media 160 that facilitates conversion of an incoming $NO_2$ gas delivered to the inlet 140 to an outgoing NO gas exiting at the outlet 190.

Figure 3A:
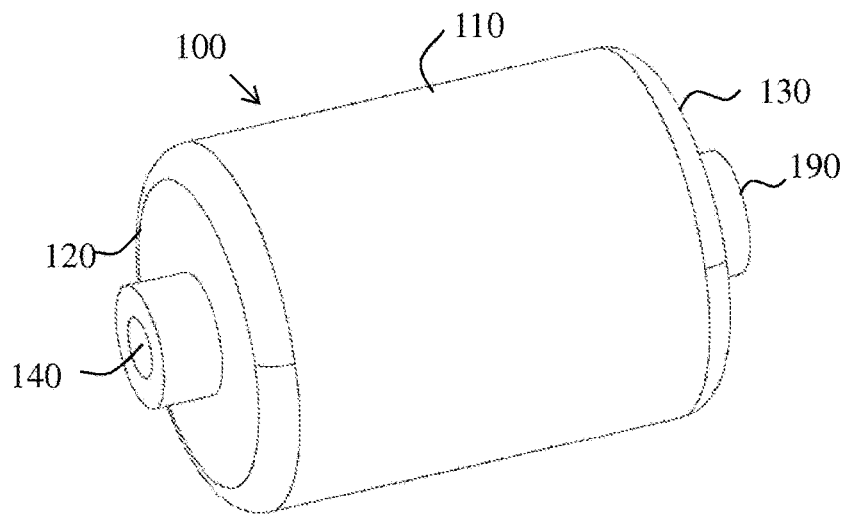
FIGS. 3A-3C illustrate another exemplary $NO_2$—NO conversion reactor, in accordance with exemplary embodiments of the present invention.
Figure 3B:
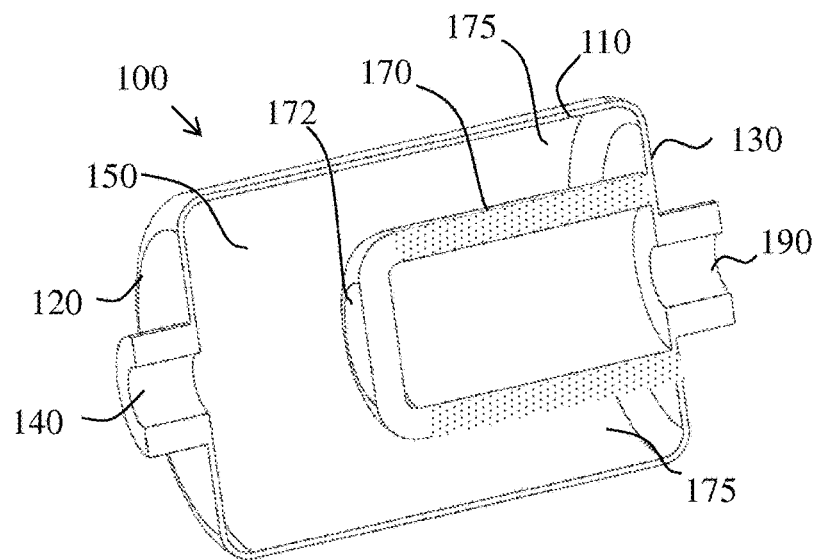
Figure 3C:
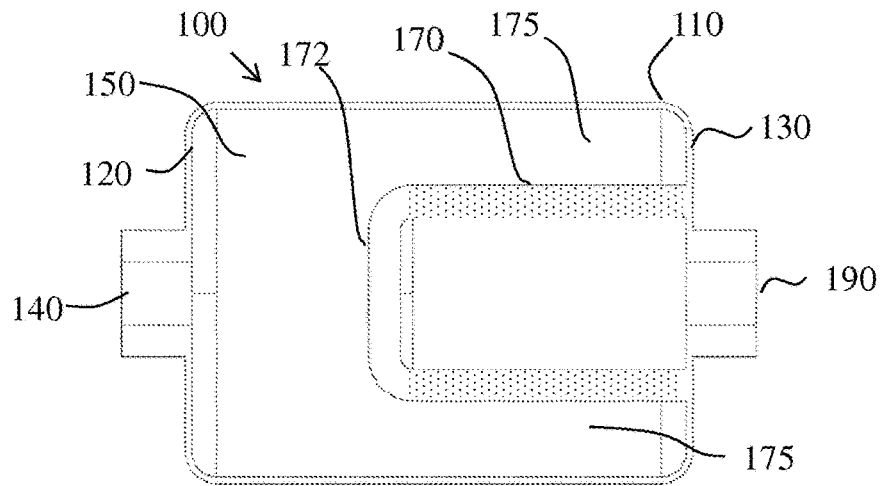

Referring to FIGS. 3A-3C, a general example of porous solid-type $NO_2$-to-NO reactor cartridge 100 is illustrated. Differing from the above described packed-type $NO_2$-to-NO reactor cartridge, the consumable conversion media for the porous solid-type $NO_2$-to-NO reactor cartridge 100 is a coated porous, bonded or sintered structure, for example a glass frit or sintered silica gel, in the form of a cylindrical wall 170 to provide a surface area for coating with the consumable reactant, for example ascorbic acid and water. An example of a sintered silica gel is described in U.S. Pat. No. 3,397,153 A issued Aug. 13, 1968, to Sippel et al., and incorporated herein by reference in its entirety.

Still referring to FIGS. 3A-3C, a first end of the cylindrical wall 170 may be capped with an end wall 172 of similar porous material or closed off with a non-porous disk. The second end of the cylindrical wall opposite the first end may be affixed to the outlet end wall 130, such that the cylindrical wall 170 surrounds the outlet 190. Gas entering the conversion reactor 100 through the inlet 140 enters the internal volume 150 of the reactor body including the gap 175 between the annular wall 110 and the porous cylindrical wall 170, and is forced through the porous cylindrical wall 170 under pressure. The porous cylinder wall 170 is affixed to the outlet end wall 130 in a manner that prevents gas from penetrating between the cylindrical wall and end wall, as would be known in the art of bonding technology, so all of the gas exiting the cylinder has to pass through the porous cylindrical wall 170. A porous cylindrical wall coated with consumable reactants forms a monolithic consumable conversion media in contrast to a packed consumable conversion media, wherein monolithic refers to a structure having a defined shape and determinable dimensions in contrast to a packed material formed by a large number of separate particles that flow if not retained within a volume.

Although reference has been made to a cylindrical wall, other shapes including but not limited to oval, elliptical, quadrilateral, polygonal, are also contemplated and intended to fall within the scope of the invention.

In various embodiments, the consumable conversion media, therefore, can be a cylindrical wall or a packed bed coated with the consumable reactants. The reactant gas (e.g., $NO_2$), may become absorbed onto the coated surface (e.g., silica gel) and interact with the consumable reactants (e.g., ascorbic acid and water) to produce a product gas (e.g., NO), which desorbs from the surface of the consumable conversion media and is transported out of the conversion reactor by a carrier gas, which may be non-reactive (e.g., $N_2$), reactive (e.g., $O_2$, $H_2O$), or a combination thereof (e.g., air).

It will be understood that the cross-sectional shape of $NO_2$-to-NO reactor cartridges, and elements thereof, can be any reasonable cross-sectional shape such as, but not limited to, round, ovoid, quadrilateral, and polygonal, to name a few. For ease, the cross-sectional shape of $NO_2$-to-NO reactor cartridges, and elements thereof, is described as being round, or variations thereof. This is merely for ease and is in no way meant to be a limitation.

With an understanding of the delivery systems and $NO_2$-to-NO reactor cartridges, principles and embodiments of the present invention relating to systems and methods of determining the remaining useful life of a $NO_2$-to-NO reactor cartridge and/or a break-through of $NO_2$, and providing an indication of the remaining useful life and/or break-through can now be shown, for example, in greater detail. It will be understood that various embodiments can be used, modified, and/or be affiliated with systems for NO inhalation therapy that can include an initial source of gas that is NO and/or $NO_2$.

In exemplary embodiments, the remaining useful life of $NO_2$-to-NO reactor cartridge can be determined and/or provided to users in one or more meters, such as dosage meters. In exemplary embodiments, meters can be integral with and/or operatively associated with a $NO_2$-to-NO reactor cartridge.

In exemplary embodiments, meters can include and/or be operatively associated with one or more sensors, which in turn may be operatively associated with at least a portion of the conversion reactor. Sensor can be, but is not limited to, a flow sensor, a spectrophotometric sensor, a chemical sensor, an electrochemical sensor, a pH sensor, a moisture sensor, or a combination of one or more sensors.

The meter can be internal to the reactor or external to the reactor depending upon the particular capabilities and requirements of the monitoring method. In some embodiments, the methods of monitoring a performance characteristic require a device in contact with the gas, the consumable conversion media, or the reactor body, for example, electrochemical monitoring. In other embodiments, the method of monitoring the performance characteristics may allow remote detection of physical or chemical property or attribute, for example, spectrophotometric analysis such as UV/VIS or FTIR analysis. In various embodiments, an electronic signal generated by the meter can be communicated over a communication path to a microprocessor-based system to interpret the signal as a representative value.

The microprocessor-based system also referred to as a computer, can be a single board computer, a laptop computer, a desktop computer, a server, a mainframe, a pad, a tablet, an application specific integrated circuit (ASIC), or other analog and digital electronic circuitry known in the art. The microprocessor-based system may be configured to receive the electronic signals and perform data acquisition, which may be used for subsequent calculations and determinations. A microprocessor-based system may comprise transitory and non-transitory memory for storing programs, acquired data, and calculated values as would be known in the art. The microprocessor-based system may be configured to communicate and interact with the various meters, spectrometers, and devices described herein.

Principles and embodiments of the present invention also relate to determining the activity of the consumable conversion media, the concentration of various components in the gas stream at various locations in the system, or both. Consumable conversion media components of interest can include ascorbic acid, dehydroascorbic acid, nitric acid, water, or combinations thereof. Gasses of interest can include $NO_2$, $NO$, and $O_2$, or combinations thereof.

Principles and embodiments of the present invention also relate to identifying sample points located within a reactor cartridge and/or an inhalation therapy system consisting of at least one reactor cartridge, and placing one or more sensor probes into the reactor cartridge and/or inhalation system, wherein one or more sensor probes may be placed at each of the one or more sample points to monitor the various reactants employed in the system. Sensor probes located at sample points may provide particular, relevant information about the concentration of consumable reactants, gaseous reactants, gaseous products and any combination thereof. The sensor probes may be connected to meters, spectrometers, and other devices through wires and/or wirelessly (e.g., RF, optical, blue tooth, etc.) and connectors as known in the art.

In embodiments, a sensor probe may be suitably configured and adapted to perform any of the chemical and physical measurements described herein, for example, a spectrophotometric sensor probe (e.g., an optical fiber, a window), fluorescence probe, an electrochemical sensor probe (e.g., carbon nanotube), a pH sensor probe (e.g., a micro pH electrode), a chromatography sample probe (e.g., a glass or plastic cannula), or a temperature sample probe (e.g., thermistor, thermocouple), and may be provided within a conversion cartridge or inhalation system. A sensor probe may be combined with a suitable chemical reactant (e.g., color-active agent, a sensitizing reagent, chemical indicator) to facilitate or increase sensitivity of the analytical method to the other reactants of interest.

The sensor probe(s) in combination with a suitable operatively associated meter and/or suitable chemical reactant is a means for monitoring the functioning of the conversion reactor and determining a lifetime. The sensor probe(s) provide a means for chemically and/or physically sampling the conversion reactor, and include an optical fiber, a window, a carbon nanotube, a micro pH electrode, a cannula, a thermistor, a thermocouple, alone or in combination with a color-active agent, a sensitizing reagent, a chemical indicator.

The meter, including spectrometers, gas chromatographs, voltmeters, ammeters, pH meters, and flow meters, provides a means of measuring the physical and/or chemical characteristic(s) sampled by a sensor probe and/or chemical reactant from the conversion reactor, and generating values of the physical and/or chemical characteristic(s) that indicate the level of functioning of at least a portion of the conversion reactor.

In embodiments of the present invention, sample points can be identified at various locations along the axial length of the $NO_2$-to-$NO$ reactor cartridge, which can be quantitatively associated with the conversion reactors $NO_2$-to-$NO$ performance, as well as the depletion of the consumable reactants, such as ascorbic acid and/or water, and the accumulation of the consumable reactant inactive materials, such as dehydroascorbic acid and nitric acid. As the consumable reactants on the packing material are used up, the reactant gases can expect to experience a reduced amount of surface area within the conversion reactor capable of converting $NO_2$ to $NO$. Calibrations relating the concentration to performance can be accomplished through reactor sampling and statistical analysis, as would be known in the art of manufacturing and quality control. In exemplary embodiments, measurement of relative concentration of ascorbic acid and/or dehydroascorbic acid, and/or water, on the silica gel surface along the longitudinal gas flow path can be an indication of reactor life time and/or performance.

In embodiments of the invention, locations within the conversion reactor that can provide specific information relating to the functioning of the consumable conversion media and consumable reactant activity of the reactor can be identified. These locations may be positioned along the length of the reactor and/or packing material in reference to the direction of gas flow, such that a sensor positioned at the entry location is positioned at a leading edge of consumable conversion media closest to the inlet of the conversion reactor, and is therefore the first sensor to detect incoming gas or reaction products of an incoming gas. A sensor positioned at the outlet location is positioned at a trailing edge of consumable conversion media closest to the outlet of the conversion reactor, and is therefore the last sensor to detect incoming gas or reaction products of an incoming gas.

In embodiments, there will generally be longitudinal gas flow along the axis of the conversion reactor from an inlet to an outlet, and there may be radial flow away from an inlet and/or reactor axis towards the walls of the conversion reactor, as would be known in the art.

Figure 4:
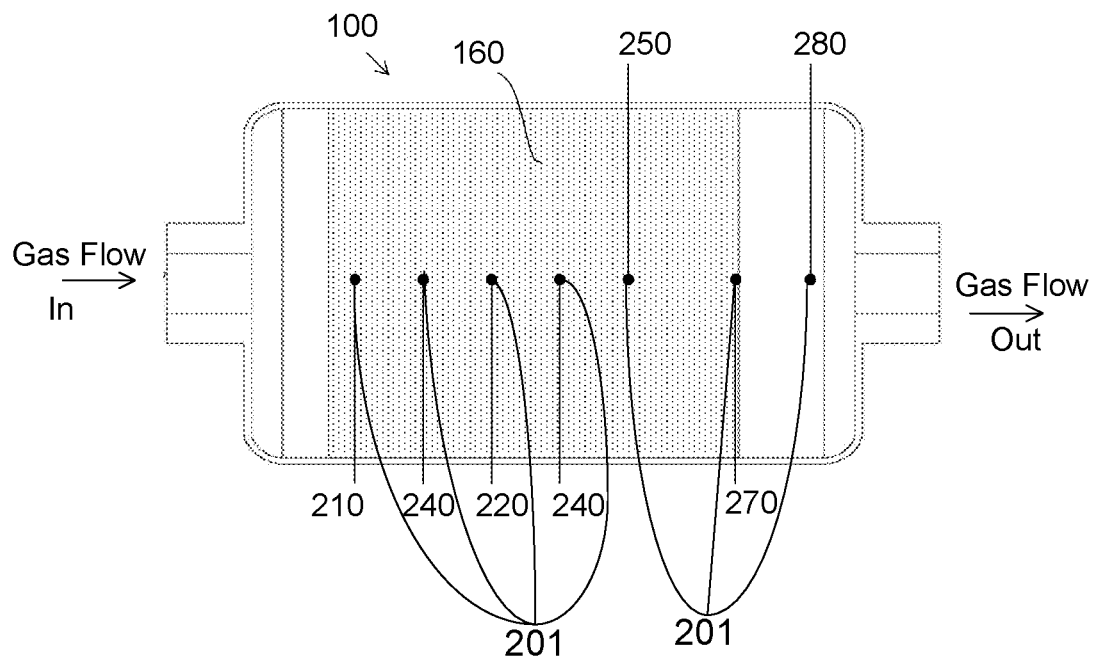
FIG. 4 illustrates an exemplary $NO_2$—NO reactor cartridge with integrated sensor probes, in accordance with exemplary embodiments of the present invention.

FIG. 4 illustrates a non-limiting example of a plurality of sensor probes 201 that may be positioned within the internal volume 150 of a conversion reactor 100, and may be operatively associated with the consumable conversion media 160, inlet 140, and/or outlet 190 of the reactor 100. In the example, the locations can include an entry sample point 210 located at the front end of the packing material, which may be at a leading edge of consumable conversion media 160 closest to the inlet 140, an exit sample point 280 located at the back end opposite the front end of the packing material, which may be at a trailing edge of consumable conversion media 160 closest to the outlet 190, a mid sample point 220 half way between the front end and back end of the packing material. The locations can include for example one or more intermittent sample points 240 located at various distances between the front end and back end of the reactor, where such intermittent sample points may have fixed or varying distances between them along the axis of the reactor. The sensor locations can also include a cautionary sample point 250 positioned a predetermined axial distance from the trailing edge of consumable conversion media, that is determined by the mean free path of a gas molecule traveling through the consumable conversion media.

In exemplary embodiments, the distance from the trailing edge of consumable conversion media 160 can be determined from the statistical number or percentage of unreacted gas molecules (e.g., $NO_2$) that would traverse the distance without conversion to a product molecule (e.g., NO), where the number may be set at an absolute concentration such as 0.1 ppm $NO_2$, or a percentage may be set at a relative amount such as 1% of $NO_2$ entering the reactor. Additional sensor locations may be positioned at other sample points of interest, such as along the periphery of the packed material to detect channeling, buried to different depths within the consumable conversion media to detect conversion fronts, and/or at the gas inlet or gas outlet to detect gas concentration(s) before or after interaction with the consumable conversion media.

Figure 5:
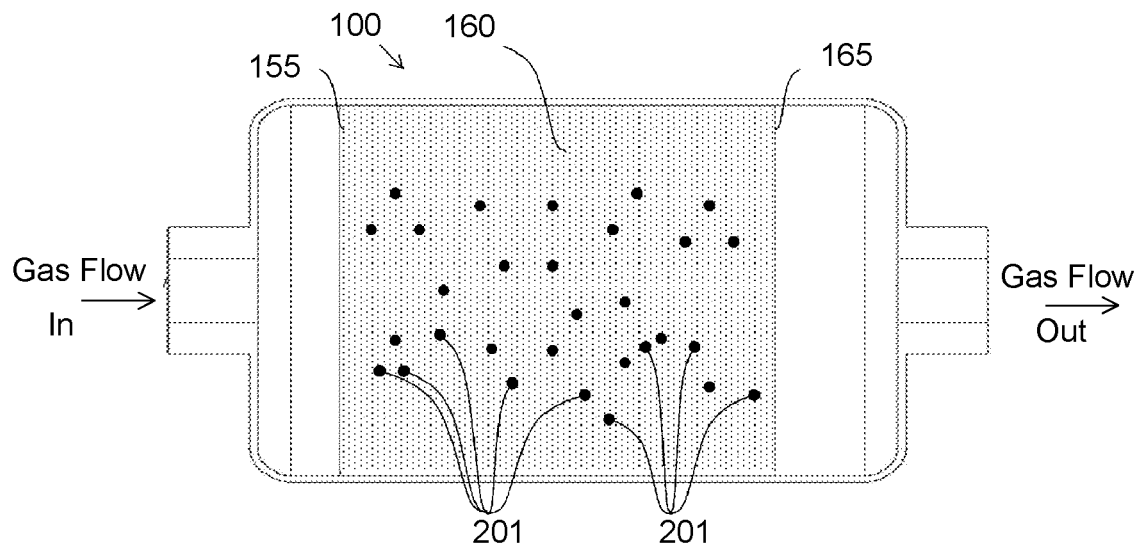
FIG. 5 illustrates an exemplary $NO_2$—NO reactor cartridge with integrated sensor probes, in accordance with exemplary embodiments of the present invention.

FIG. 5 illustrates a perspective view of a conversion reactor 100 indicating the intended direction of gas flow through the internal volume 150 and packed consumable conversion media 160. In the embodiment illustrated in FIG. 5, the packing material may be held within a portion of the internal volume by a front end retainer 155 positioned nearer the inlet 140 and a back end retainer 165 opposite the front end retainer 155 and positioned nearer to the outlet 190 of the reactor. There may be a gap between the inlet end wall 120 and the front end retainer 155 that does not contain any packing material and forms an open internal volume at the inlet 140. There may also be a gap between the outlet end wall 130 and back end retainer 165 that does not contain any packing material and forms an open internal volume at the outlet 190.

In the non-limiting example illustrated in FIG. 5, the sample probes 201 are buried within the consumable conversion media 160 to a predetermined depth, so that the probes may not be in contact with the annular wall 110 of the reactor. In the illustrated embodiment, a plurality of sensor probes 201, for example six (6), are arranged in a hexagonal pattern an equal distance from the front end retainer 155. An additional set of six probes 201 arranged in a second hexagonal pattern may be located an equal distance from the probes located closest to the front end retainer 155. Similarly, a third set of probes 201 arranged in a third hexagonal pattern may be located an equal distance from the second set of probes, as may additional fourth, fifth, etc., sets of probes. Each set of probes may be arranged in the same radial plane, which can be perpendicular to the reactor axis and intended axial gas flow.

Figure 6:
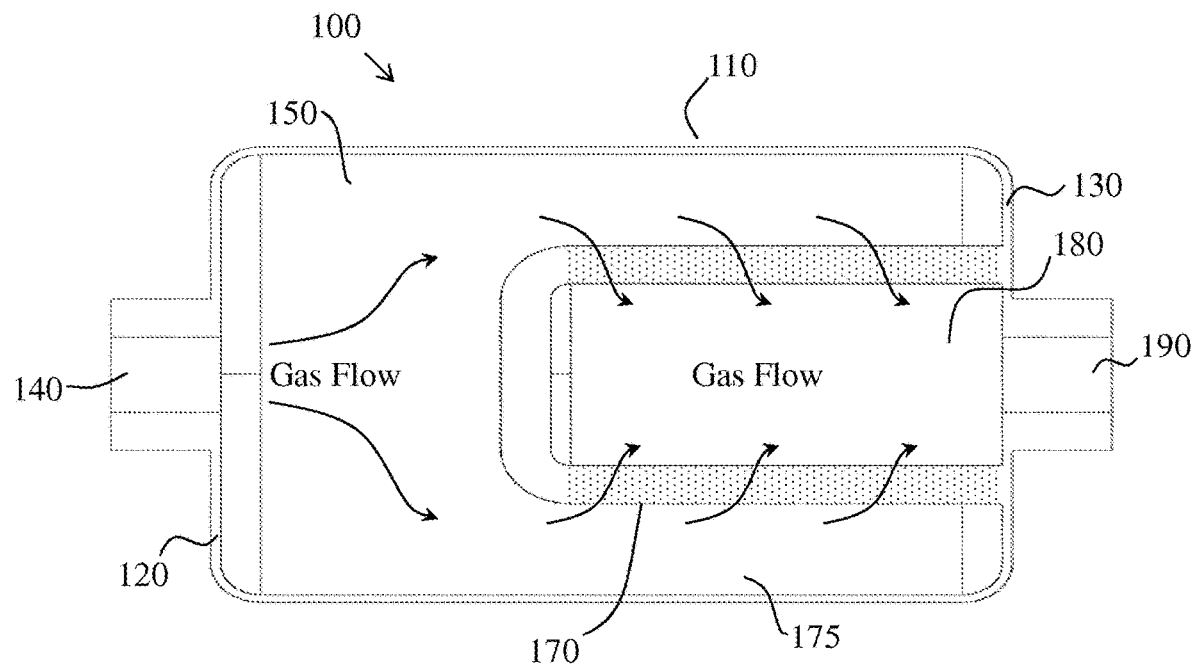
FIG. 6 illustrates an exemplary $NO_2$—NO reactor cartridge with a monolithic consumable conversion media, in accordance with exemplary embodiments of the present invention.

FIG. 6 illustrates a perspective view of a conversion reactor 100 indicating the intended direction of gas flow through the internal volume 150 and cylindrical wall 170 of the monolithic consumable conversion media. The gas enters through the inlet 140 and passes through the internal volume 150 and gap 175 to the monolithic consumable conversion media, which can be semi-permeable. The gas passes through the porous cylindrical wall 170 of the semi-permeable, monolithic, consumable conversion media into the hollow space 180 and out through the outlet 190. $NO_2$ gas passing through a consumable reactant coated cylindrical wall 170 can be converted into NO through interaction with consumable reactants (e.g., ascorbic acid and $H_2O$) on the surfaces. In exemplary embodiments, the thickness of the cylindrical wall should be greater than the mean free path of the gas through the porous wall material to ensure all of the $NO_2$ interacts with a consumable reactant coated surface before reaching the hollow space 180.

While the direction of gas flow has been illustrated as from the exterior of the semi-permeable wall 170 into the interior hollow space 180, in embodiments the direction may be reversed without departing from the spirit and scope of the invention.

Figure 7:
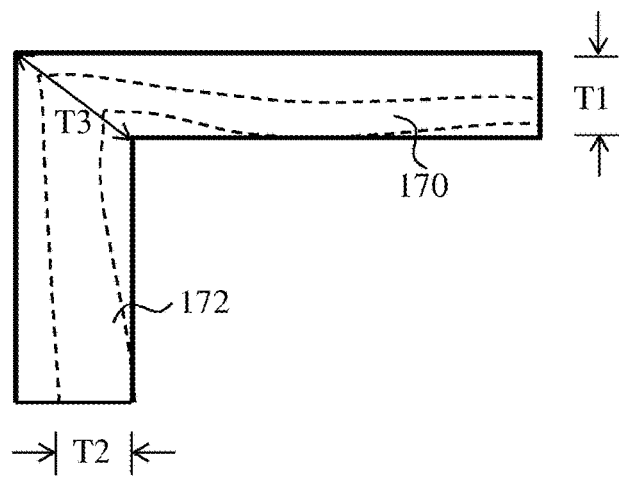
FIG. 7 illustrates a close-up view of exemplary monolithic consumable conversion media, in accordance with exemplary embodiments of the present invention;\

A close-up view of a porous cylindrical wall 170 with an end covered with the same porous material is illustrated FIG. 7, which shows a thickness T1 of the cylindrical wall 170, a thickness T2 of the end cover, and a thickness T3 at a corner formed by the cylindrical wall and end cover. Where the relationships between the thicknesses are T3>T1, T3>T2, and T1 can be greater, equal, or less than T2. Gas passing from one side of the cylinder to the other travels a distance D through the porous material, where D is greater than or equal to the smallest thickness. In embodiments in which the porous cylindrical wall is coated with a consumable reactant(s) (e.g., ascorbic acid, $H_2O$) and exposed to a reactant gas (e.g., $NO_2$), the consumable reactant is used up over time.

Also as illustrated in FIG. 7, the ongoing flow of reactant gas through the coated walls generates a conversion front 310 in which the reactant components have been essentially depleted (e.g., consumed) on one side of the front and are still sufficiently active on the other side of the front. In the non-limiting example, the conversion front will advance through the consumable conversion media as more and more of the reactant components are exhausted, until the reactant gas, $NO_2$, begins to pass through the wall(s) without conversion to the product gas, NO. The conversion front may advance a distance into the wall thickness T1 and T2 by time t1, and a greater distance by time t2, such that the $NO_2$ passes through the porous cylindrical wall without conversion to NO at one or more points around the cylindrical wall 170 and end wall 172.

In embodiments of the invention, the total area of the cylindrical wall 170 and end wall 172, calculated as $A = 2 \cdot pi \cdot rh + 2 \cdot pi \cdot r2$, where h is the length of the cylindrical wall and r is the radius of the cylindrical wall, is greater than the circular area of a front face of packed consumable conversion media 160, so the possible location of a channel in the cylindrical wall is greater. The number of probes required to detect channeling may therefore be greater for the cylindrical wall consumable conversion media 170 than for a packed consumable conversion media 160.

Figure 8A:
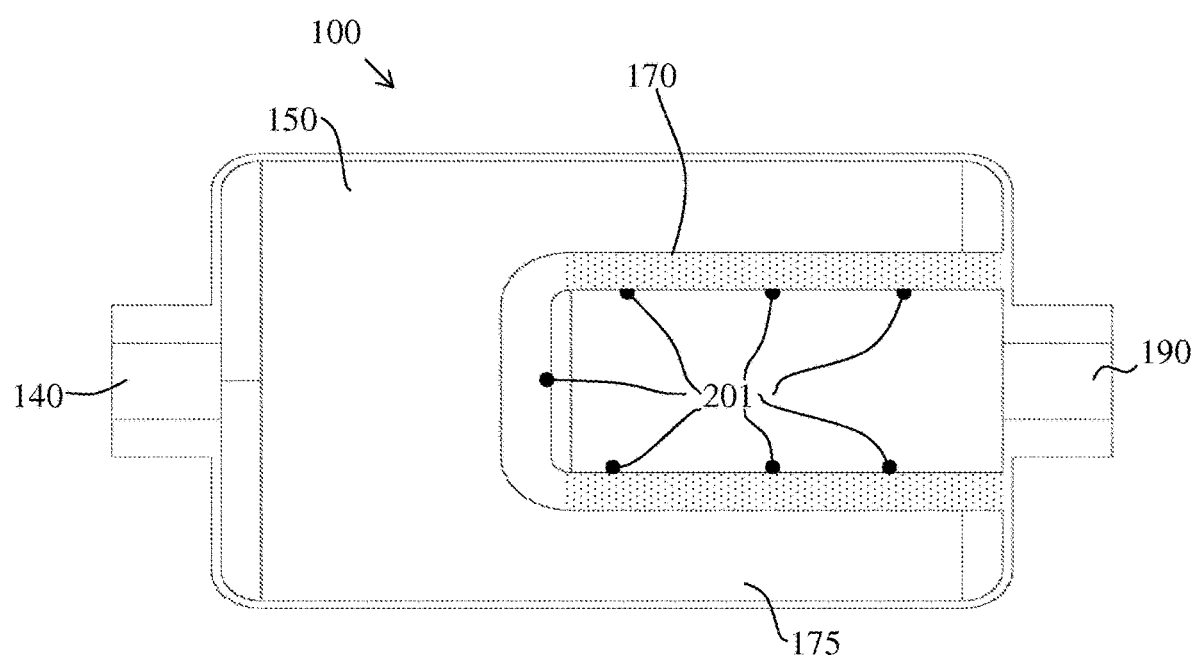
FIGS. 8A-8C illustrate exemplary $NO_2$—NO reactor cartridges with integrated sensor probes, in accordance with exemplary embodiments of the present invention.

In embodiments illustrated in FIG. 8A, sensor probes 201 may be placed along the internal side of the cylindrical wall 170 to monitor the consumable conversion media components of interest. The sensor probes 201 may be embedded within the cylindrical wall or affixed to the internal surface of the cylindrical wall 170, or both. The sensor probes may monitor the consumable conversion media components of interest and/or the gases of interest, and communicate electric signals to an electric circuit (i.e., meter) that measures the amounts detected and may communicate the amounts to a computer as an electrical signal for comparison with established threshold values.

Figure 8B:
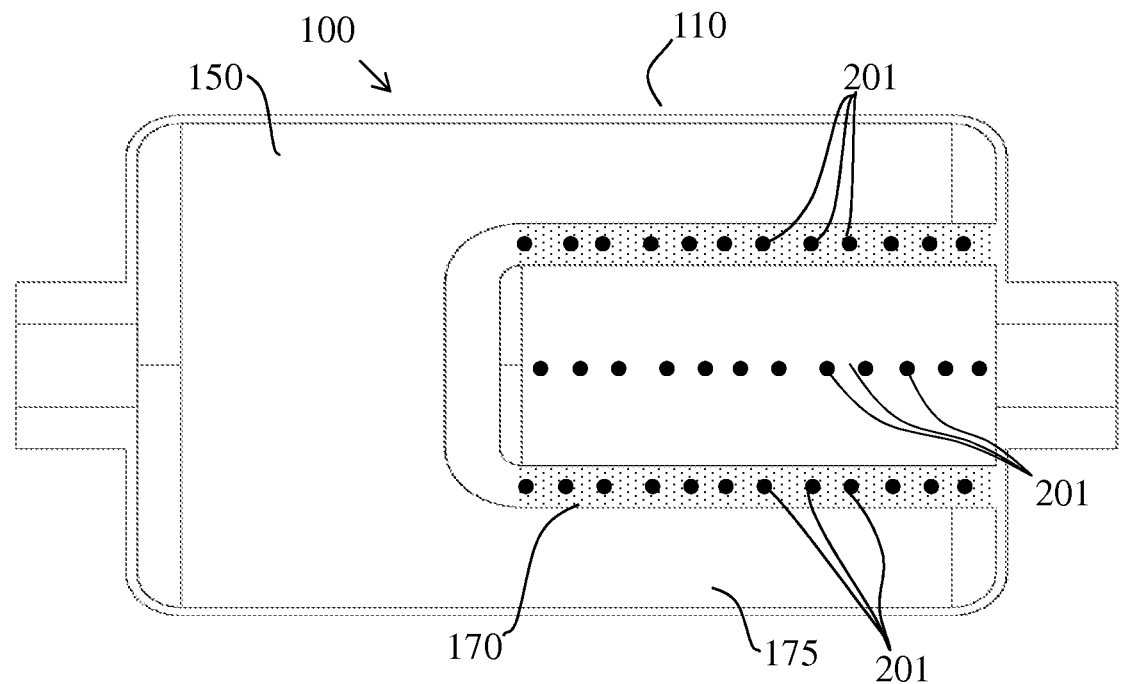

In embodiments illustrated in FIG. 8B, sensor probes 201 may be placed in a row within the cylindrical wall 170, wherein the sensor probes may be arranged as a linear array along at least a portion of the length of the cylindrical wall 170. An axial array may be placed on one or more sides of the cylindrical wall 170 to determine if the consumable conversion media is being depleted evenly on different sides of the cylindrical wall 170. As a non-limiting example, the sensor probes may be single-wall carbon nanotubes with manganese-porphyrin, which may be nitrogen dioxide selective sensors based on amperometric changes as disclosed in Popescu M et al. Sensor of Nitrogen Dioxide Based on Single Wall Carbon Nanotubes and Manganese-Porphyrin. Digest Journal of Nanomaterials and Biostructures Vol. 6, No 3, July-September 2011, p. 1253-1256, incorporated herein by reference in its entirety.

In embodiments, sensor probes 201 may be placed around the circumference of the cylindrical wall 170, where the sensor probes form a circular array.

Figure 8C:
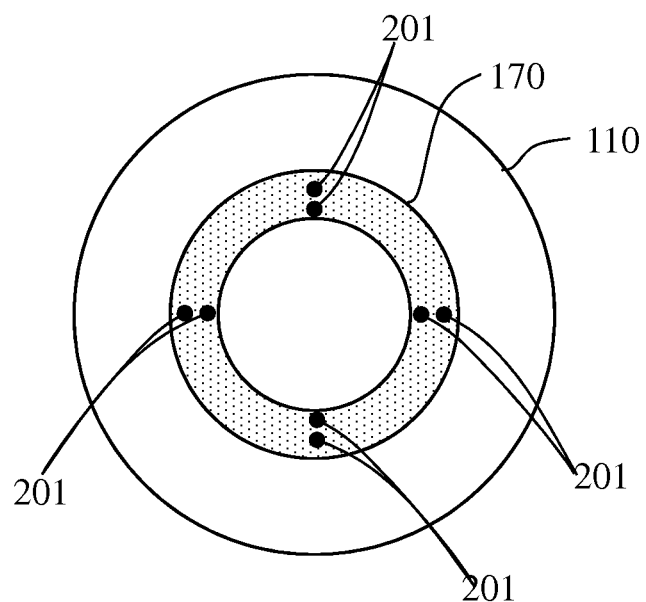

In embodiments illustrated in FIG. 8C, the probes 201 may be placed radially within the cylindrical wall 170, where one or more sensor probes are placed at different distances from the exterior surface of the cylindrical wall 170 to determine if the gases are passing uniformly through the wall thickness.

Figure 9:
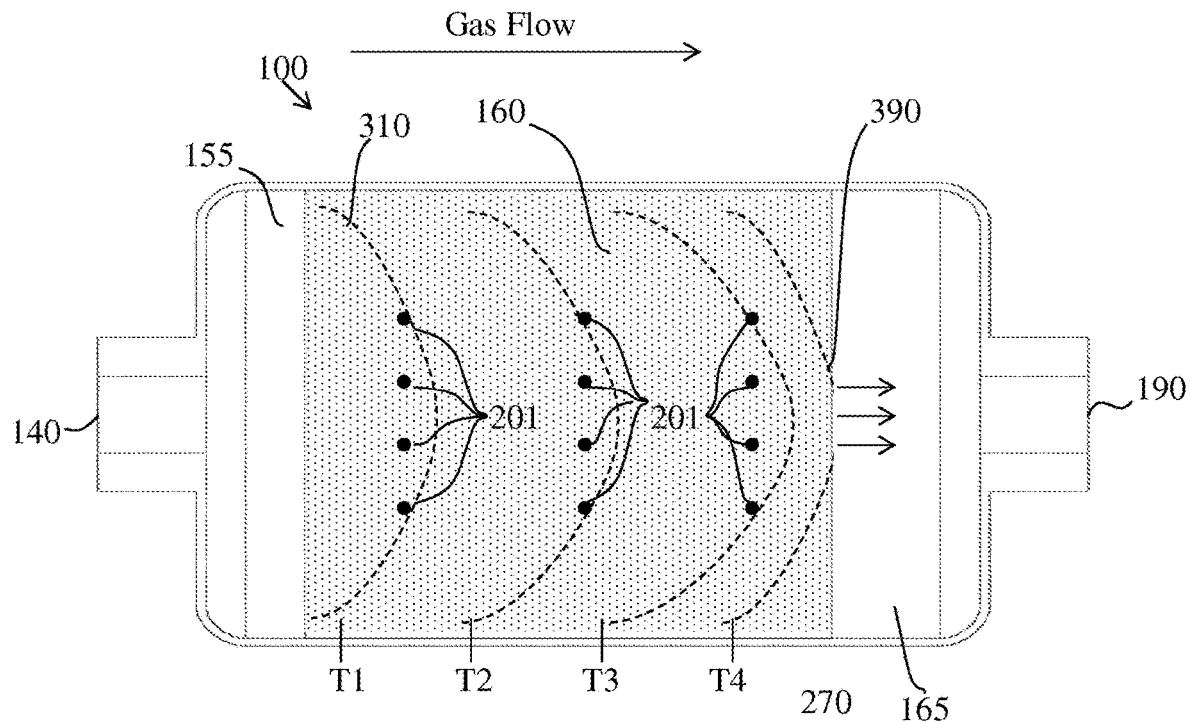
FIG. 9 illustrates an exemplary $NO_2$—NO reactor cartridge with integrated sensor probes, in accordance with exemplary embodiments of the present invention.

FIG. 9 illustrates a hypothetical flow of gas from the inlet 140 through the consumable conversion media 160 held in place by a front end retainer 155 and back end retainer 165. As illustrated in the example, source gas, for example $NO_2$, may enter the inlet 140 at an initial time zero t0, and advance through the consumable conversion media, where the $NO_2$ interacts with the consumable conversion media. The consumable conversion media becomes exhausted by the reaction with the incoming gas, such that $NO_2$ entering the consumable conversion media 160 passes through a detectable distance by some later time t1, without conversion to the product gas, for example NO. The exhaustion of the consumable conversion media or presence of a gas of interest may be detected by a set of sensor probes 201 located at the first distance from the front end retainer 155 (also shown in FIG. 5).

In the illustrated example, the sensor probes 201 at the conversion front indicate when the consumable conversion media between the front end retainer 155 and first arrangement of probes 201 is no longer active. Similarly, at some later time t2, the second arrangement of probes 201 indicate that the $NO_2$-to-NO conversion front has advanced the additional distance between the first and second sets of sensor probes 201, and again for an even later time t3. At an even later time t4, the majority of consumable conversion media has been used up and at least a portion of the $NO_2$ entering the inlet can pass through the consumable conversion media 160 and exit the reactor unconverted. This passage of at least a portion of the entering $NO_2$ through the conversion reactor unconverted to NO is referred to as break-through. The length of the packed region of the reactor that becomes unreactive at the time of initial break-through can be determined experimentally and/or theoretically, and an arrangement of sensor probes can be positioned the determined length from the front end retainer 155 or back end retainer 165 to detect when break-through is imminent to protect a recipient from a toxic dose of $NO_2$.

As can be appreciated, reliance on experimental and theoretical information (e.g., average life-time, calculated points of break-through) can fail to account for real-life deviations from a hypothetical expected or optimum performance. It can be extremely difficult to account for all the potential failure modes of a consumable cartridge, some of which are presented in at least the various exemplary scenarios described herein, using high level averages and broad modeling assumptions. Importantly, appropriately located sensor probes can be used to determine actual reactor cartridge lifetime by taking real-time measurements, which can take manufacturing and performance deviations directly into account, and/or provide users with lifetime information, for example, in a meter to at least increase patient safety and efficacy.

Figure 10:
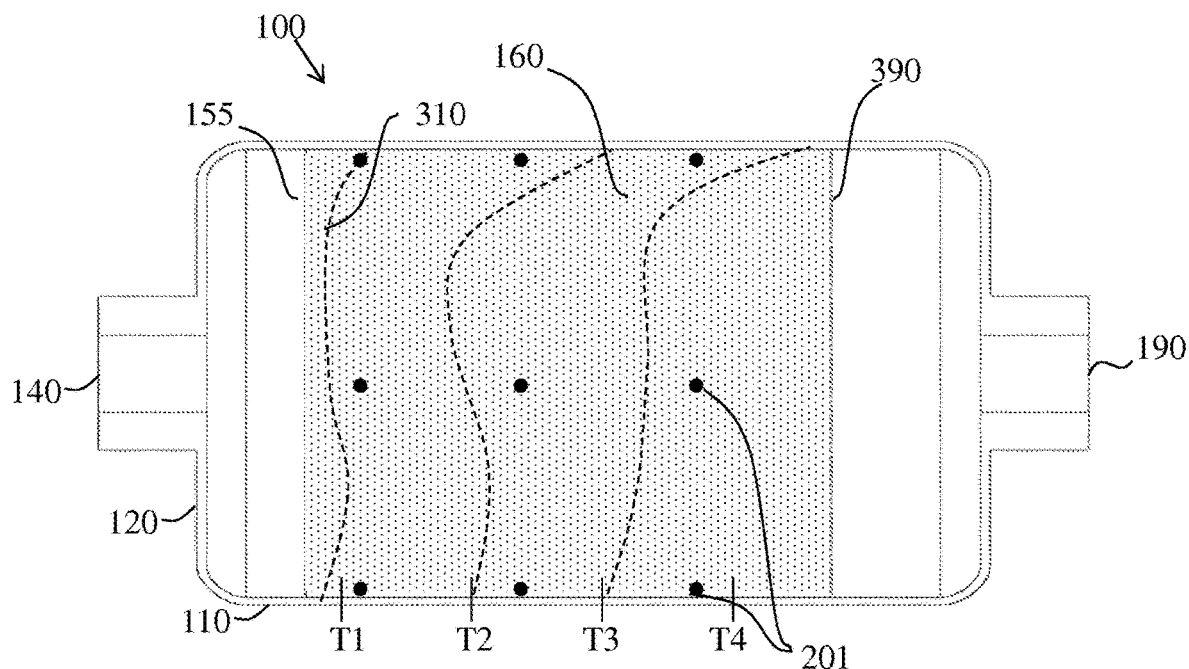
FIG. 10 illustrates an exemplary $NO_2$—NO reactor cartridge with integrated sensor probes, in accordance with exemplary embodiments of the present invention.

FIG. 10 illustrates an example of channeling along an outer edge of consumable conversion media 160 adjacent to an annular wall 110 of the conversion reactor 100. In the illustrated example, the $NO_2$-to-NO conversion front 310 may advance more quickly at the interface between the coated packing material and annular wall 110 due to looser packing and/or settling of the packing material from vibration in transportation and handling, mechanical shock, aging and deterioration of the material's physical integrity. As shown in the example, the conversion front 310 no longer propagates primarily through the bulk of the consumable conversion media, but advances along an outside edge. In an embodiment, the sensor probes 201 can be positioned around the periphery of the consumable conversion media 160 adjacent to the inside surface of the annular wall 110 to detect such channeling.

For example, a first set of four (4) sensor probes may be arranged in the same radial plane around the periphery of the consumable conversion media 160 with one (1) probe located in each quadrant of the conversion reactor. The first set of four sensor probes may be located at a predetermined distance from the front end retainer 155 or the inlet end wall 120. A second set of four sensor probes may be located at a predetermined distance from the front end retainer 155 or the first set of sensor probes. Similarly, a third set of four sensor probes 201 may be located at a predetermined distance from the front end retainer 155 or the second set of sensor probes.

As shown in FIG. 10, the conversion zone 310 may advance farther in one quadrant of the consumable conversion media (e.g., the upper section) faster than in the other three quadrants, so that at time t1 the sensor probe 201 in that quadrant detects exhaustion of the consumable conversion media even though the other three probes still indicate the consumable reactants are active. By time t2, the conversion front 310 has already propagated past the probe 201 in the upper quadrant, while the remaining three probes in the second set still indicate the consumable reactant's activity. By time t3, $NO_2$ break-through has just occurred in the compromised quadrant by the time the last probe in the second set indicates exhaustion of the consumable conversion media in that quadrant.

In embodiments of the invention, the progression of the consumable reactant exhaustion along a particular path can be mapped to determine that at least particular sections of the reactor may be compromised, as well as when break-through may be expected, and provide a warning to a user that replacement of a reactor is necessary.

In various embodiments, a combination of sensor probes may be arranged both within the bulk and around the periphery of the consumable conversion media to monitor an expected propagation of the conversion front and determine if channeling is occurring in the consumable conversion media.

While the above embodiments and examples referred to specific numbers and geometrical arrangements of the sensor probes, it is understood that other quantities and arrangements of the probes are contemplated and may be used without departing from the spirit and scope of the invention.

A sensor probe may be one or more component(s) that undergo a chemical or physical change due to interaction with a gas of interest or consumable conversion media component of interest, for example one or more carbon nanotubes embedded in the consumable conversion media with electrical wires from the nanotube(s) to an external connector on the reactor body. The sensor probes may also be a device operatively associated with a reactor that communicates a detectable signal from a location within the reactor's internal volume to a measuring device (e.g., meter) remote from the reactor, for example, a fiber optic line that receives light signals from a volume of gas or surface area and transmits the signal to a spectrophotometer for UV/VIS/IR analysis.

It will be understood that principles and embodiments described with reference to porous solid-type $NO_2$-to-NO reactor cartridges, and elements thereof, and principles and embodiments described with reference to packed-type $NO_2$-to-NO reactor cartridge, and elements thereof, can, when applicable, be implemented in either configuration. For example, at times, sensor probes, sample points, sensors, and the like are described with reference to porous solid-type $NO_2$-to-NO reactor cartridges, and elements thereof, such as cylindrical wall, cylindrical wall consumable conversion media, consumable conversion media, etc. or are described, at times, with reference to packed-type $NO_2$-to-NO reactor cartridge, and elements thereof, such as packed consumable conversion media, consumable conversion media, etc. This is merely for ease and is in no way meant to be a limitation. Accordingly, reference made to one type of reactor cartridge or another, at times, is made for ease and is not meant to be limited to that type of reactor cartridge.

Principles and embodiments of the present invention relate to measuring the color change of a reactant that chemically interacts with one or more gas(es) of interest to determine the amount of gas present. In an embodiment, the gas of interest is $NO_2$, and the reagent chemically reacts with the $NO_2$ in a manner that results in a color change of the reactant. The color change may be determined visually by an observer or user, or the color change may be detected spectrophotometrically, for example by a device, such as a single chip spectrophotometer using micro electro-mechanical system (MEMS) technology. The extent of the color change can provide a quantitative determination of the amount of gas present in a specific volume and thereby determine a concentration. In embodiments, a spectrometer or spectrophotometer or colorimeter can output an electronic signal that can be used to determine the extent of a color change, and the signal may be communicated to a computer for display or the triggering of an alarm.

The combination of a color active agent, a fiber optic or window sample probe, and a spectrometer or spectrophotometer or colorimeter (herein referred to as a spectrometer) provides a means for monitoring the functioning of the conversion reactor and determining a lifetime of the conversion media.

In an embodiment, the color-active agent can be located within the internal volume at the outlet end of a conversion reactor in order to detect and signal the presence of $NO_2$ in the outlet gas stream. Detection of a predetermined amount of $NO_2$ in the outlet stream can be used to trigger a cut-off of gas delivery to a recipient.

Figure 11:
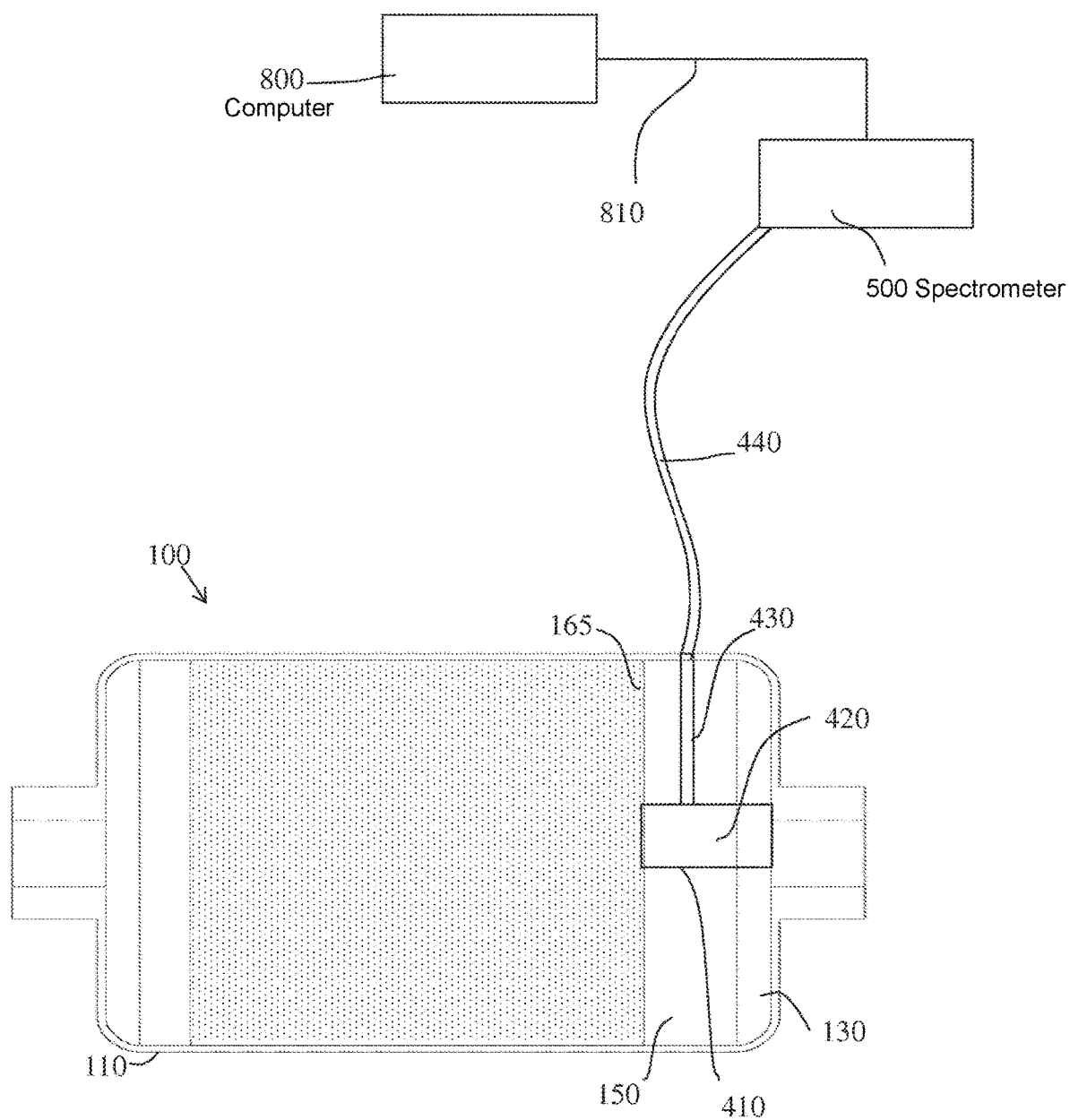
FIG. 11 illustrates an exemplary $NO_2$—NO reactor cartridge with a spectrophotometric sensor probe, in accordance with exemplary embodiments of the present invention.

In a non-limiting example illustrated in FIG. 11, a material segment 420 can be positioned in the internal volume 150 at the outlet end of the reactor 100, where the material segment 420 may be affixed to the outlet end wall 130, the back end retainer 165, the annular wall 110, or a combination thereof. The material segment 420 can be porous and coated with the color-active agent, and is located in the exiting gas flow, so that gas components impinge on the surface of the coated porous material. In an embodiment of the present invention, the color active agent coated on the surface of the material segment 420 could be o-phenylenediamine or 2,6-dichlorophenolindophenol in combination with ascorbic acid. When $NO_2$ passes through the conversion media unreacted, the $NO_2$ reaches the outlet end of the reactor and interacts with the color active agent indicating $NO_2$ is leaving the cartridge. A fiber optic sensor probe 430 can be inserted into the reactor 100 through an opening in the annular wall 110 of the body, and configured to receive a signal from at least one surface of the coated porous material 410. Impinging light from a radiant source having an acceptable spectrum could be supplied by the same fiber optic line 440 or another fiber optic line (not shown). The fiber optic line 440 can receive light reflected off of the color-active agent and communicate the light to a spectrometer 500 for wavelength detection and intensity measurement, for example absorbance or fluorescence, as would be known in the art of spectroscopic analysis. Detection of a characteristic absorbance spectra due to a sufficient color change to indicate the presence of particular gas components (e.g., $NO_2$) could be communicated to a computer 800 for display, triggering an alarm, or both. In an embodiment, the coated material 410, spectrometer 500, and computer 800 may be configured to detect a concentration of 0.1 ppm $NO_2$ or greater in the gas stream exiting the conversion reactor, or a concentration of 1.0 ppm $NO_2$ or greater in the gas stream.

In embodiments of the present invention, the color-active agent may be o-phenylenediamine which reacts with dehydroascorbic acid (DHAA) to form a tricyclic, highly fluorescent condensation product, the presence of which can be qualitatively and quantitatively determined by spectrophotometric analysis with a spectrometer or spectrometer.

Scheme 1. Reaction of o-phenylenediamine with dehydroascorbic acid (DHAA).

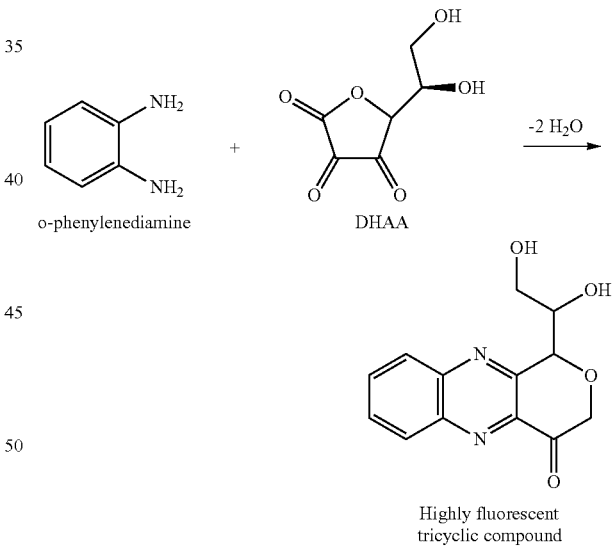

The spectrophotometer can be operatively associated with the color-active agent, and may be positioned locally with the agent, for example, with a single chip spectrometer or spectrophotometer or colorimeter mounted to the system, or remotely using a fiber optic line that communicates a light signal from the color active agent to the remote spectrometer or spectrophotometer or colorimeter.

In embodiments of the invention, the o-phenylenediamine can function as a redox sensor to detect the presence of DHAA. The presence of DHAA indicates depletion of the consumable reactant ascorbic acid and the exhaustion of the conversion reactor.

When the reactor is configured as a packed column, incoming $NO_2$ interacts with the consumable reactant's active consumable conversion media closest to the reactor inlet first. As the conversion material is used up by exposure to the $NO_2$, additional incoming $NO_2$ passes further into the packed column before reaching an active surface of the consumable reactant. This process proceeds through the packed material until $NO_2$ can pass all the way through the reactor without interacting with a consumable reactant surface. At this point $NO_2$ break-through occurs, and the reactor is effectively depleted.

Break-through may be when $NO_2$ is at a concentration of 0.1 ppm in the gas stream exiting the $NO_2$-to-NO reactor cartridge, or when the $NO_2$ is at a concentration of 1 ppm in the exiting gas stream, or the $NO_2$ is at a concentration of 5 ppm in the exiting gas stream.

In embodiments of the invention, small amounts of o-phenylenediamine can be located at discrete locations along the flow path of the gases through the packed material as redox sensors. As the consumable conversion media is depleted and the ascorbic acid becomes DHAA, the o-phenylenediamine reacts with the DHAA to form the florescent compound. This florescent characteristic can then be detected along the length of the packed column indicating how much ascorbic acid has been used up and how much active surface remains. A physical location where break-through is statistically possible due to the remaining flow path length of the $NO_2$ can be determined, and an alarm or indicator triggered to alert a user to the necessity of changing the reactor before a recipient is poisoned by toxic levels of $NO_2$.

In embodiments of the invention, the determination that break-through of the $NO_2$ is imminent can be used to actuate a regulating device to halt the delivery of at least the $NO_2$ gas to the recipient before poisoning occurs. The regulating device may cut off flow of $NO_2$ from its source, cut off gas flow exiting the conversion reactor, divert air flow around the conversion reactor to continue air/$O_2$ delivery to a recipient without NO, or divert flow of the $NO_2$/air mixture to an auxiliary conversion reactor depending upon the system configuration and therapy protocols for the recipient.

In another embodiment, the color active agent can be 2,6-dichlorophenolindophenol, (DCPIP), which is a chemical compound used as a redox dye, which when oxidized appears blue, appears pink when oxidized in the presence of acid, or appears colorless when reduced.

Scheme 2. The reduction of DCPIPH to DCPIPH2.

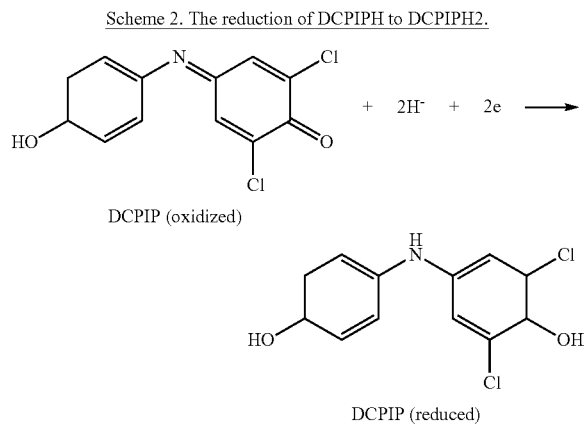

DCPIP can be used as an indicator for the presence/absence of ascorbic acid (i.e., vitamin C). If ascorbic acid (AA) is present, the blue dye, which turns pink in acidic conditions, is reduced to a colorless compound by ascorbic acid. The absence of ascorbic acid will result in the oxidized form of DCPIP, which is pink.

   [1]

   [2]

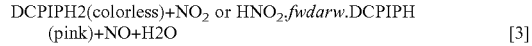   [3]

AA=ascorbic acid; DHAA=dehydroascorbic acid

Chemical reaction [1] is an acid/base reaction, while chemical reactions [2] and [3] are redox reactions. In equation [2] ascorbic acid (AA) is oxidized to dehydroascorbic acid (DHAA), and DCPIP is reduced to the colorless compound DCPIPH2. In equation [3] the colorless compound DCPIPH2 is oxidized to DCPIPH (pink) by the presence of $NO_2$ and/or $HNO_2$. Therefore the consumption (end point) of ascorbic acid will be indicated when a permanent pink color persists.

In an embodiment of the invention, a small amount of the DCPIP dye can be mixed evenly throughout the consumable conversion media. The initial appearance of the DCPIP will be colorless due to reduction of the DCPIP by the ascorbic acid. When all the ascorbic acid in the consumable conversion media is consumed by reaction with the continuous flow of $NO_2$, there will not be sufficient electrons available to keep DCPIP in its reduced form (DCPIPH2) and the consumable conversion media will then show a permanent pink color due to the formation of DCPIPH.

In an embodiment of the invention, the outer reactor shell or body of the $NO_2$-to-NO reactor cartridge can further include a transparent window that allows the color of the consumable conversion media to be physically observed by a user to determine when the DCPIP shows a pink color or representative color change. The transparent window in the body of the reactor may be made of glass, quartz, or a suitable plastic, for example polycarbonate or polyethylene terephthalate.

Principles and embodiment of the present invention also relate to determining the amount of moisture present in the consumable conversion media with a color-changing compound. A chemical compound may indicate a change in moisture content of the consumable conversion media. The chemical compound anhydrous cobalt chloride ($CoCl_2$) is blue, but it turns purple when it bonds with two water molecules to form $CoCl_2.2H_2O$. As described in the embodiments above, the $CoCl_2$ can be mixed evenly throughout the consumable conversion media. The initial color would be purple indicating that the consumable conversion media contains sufficient water to support the reaction of the ascorbic acid with the $NO_2$. However, the compound would turn blue when the water in the reactor is used up. A user could determine the reactor was no longer functioning by observing the color change through the reactor window.

Figure 12:
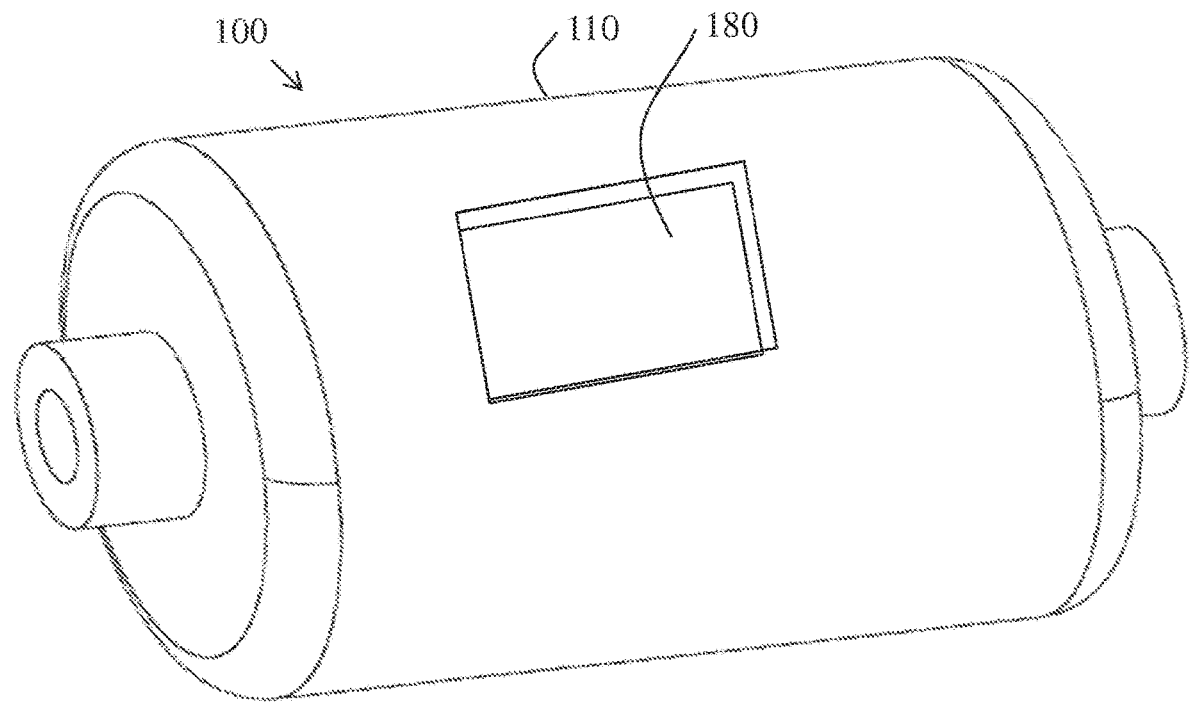
FIG. 12 illustrates an exemplary $NO_2$—NO reactor cartridge with a window, in accordance with exemplary embodiments of the present invention.

A non-limiting example of a conversion reactor 100 with a window 180 made of a material transparent to the wavelengths of interest and unreactive with the gases of interest and consumable reactant materials is shown in FIG. 12. The window may be formed in the annular wall 110 of the conversion reactor 100.

Figure 13:
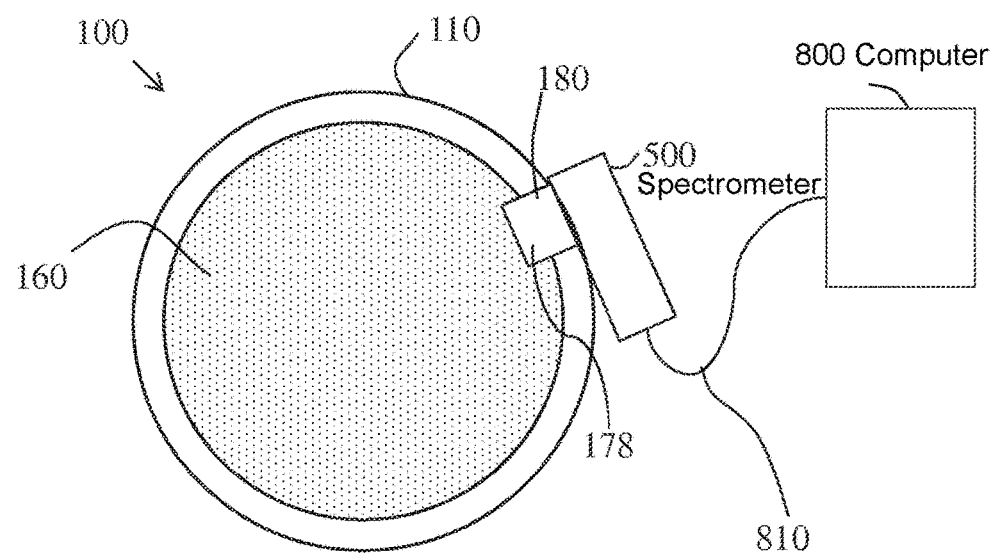
FIG. 13 illustrates an exemplary $NO_2$—NO reactor cartridge with a window and a spectrophotometric sensor probe, in accordance with exemplary embodiments of the present invention.

In another non-limiting example, illustrated in FIG. 13, a spectrometer 500 may be affixed to the outside of the conversion reactor 100 and operatively associated with the window 180 in the annular wall surrounding the consumable conversion media. A light source or broad or narrow spectrum may illuminate the consumable conversion media 160 and the spectrometer 500 may detect the spectrum and/or intensity of light reflected off of a region of consumable conversion media 160 coated with a color active agent 178, as would be known in the art. An electrical signal may be communicated from the spectrometer 500 to a computer 800 to calculate the amount of color change detected for the color active agent 178. If the computer determines that a threshold value indicating that a predetermined amount of consumable conversion media component of interest has been reached, the computer can alert a user through a display, an audible alarm, or both that the reactor is exhausted or compromised.

In a non-limiting embodiment, a spectrometer can detect the presence of oxidized DCPIP at approximately 600 nm. An electronic signal can be transmitted from the spectrometer to a computer configured for data acquisition and to determine when the absorbance at the 600 nm wavelength has changed by a predetermined amount. The computer can alert a user through a display, an audible alarm, or both that the reactor is exhausted or compromised.

In an embodiment, the trigger may be a signal from a spectrophotometric device to a microprocessor based system in electrical communication with the spectrophotometric device, where the computer then halts the flow of $NO_2$ to the recipient by sending an electrical signal to an apparatus or device regulating gas flow. A regulating device may be for example a ventilator, a valve, a pump, a diverter, a gas tank regulator, a heater shut-off, or any other device implemented in the system to generate or control a gas flow.

The regulating device, including a ventilator, a valve, a pump, a diverter, a gas tank regulator, and a heater shut-off, is a regulating means for halting the delivery of the gas to a recipient. The regulating means may be in electronic communication with a computer over a communication path, and configured to receive an actuating signal from the computer to change the state of the regulating means from a configuration in which gas can flow through the regulating means to a state in which gas cannot flow through the regulating means.

In an embodiment, the gas stream exiting the conversion reactor may be passed through a transparent tubular section containing a material that can change color relative to the absolute concentration of one or more gases of interest. A color change within the transparent tubular section may be directly observable by a user, or the color change may be detected spectrophotometrically, which communicates a signal to a readout, triggers an alarm, or actuates a flow regulation device.

In embodiments a sample of gas exiting the conversion reactor may be diverted from the delivery conduit into a side stream. The side stream of gases may be passed through the transparent tubular section containing the material that changes color, introduced into a spectrophotometer, a mass spectrometer (e.g. for determining the concentration of gases, etc.), or reaction vessels that produce a known chemical response to the gases of interest.

Principles and embodiments of the invention relate to detecting components in the gas mixture or on the consumable reactant surface directly using ultraviolet (UV), visible (VIS), or infrared (IR) spectroscopy.

In an embodiment of the invention, a fiber optic UV/VIS sensor can be positioned to detect chemical concentration at a point in the consumable conversion media along the path length of the gas flow. The UV/VIS Spectra obtained in real time from the consumable conversion media can indicate the relative amounts of ascorbic acid, dehydroascorbic acid, and nitric acid by measuring the absorbance at a suitable wavelength, for example 320 nm, 295 nm, and/or 265 nm.

In an embodiment, the Beer-Lambert Law may be applied; where, for example, a decrease in ascorbic acid on the packing material may be determined and monitored by taking repetitive measurements at approximately 265 nm. In an embodiment, an increase in dehydroascorbic acid may be determined and monitored by taking repetitive measurements at approximately 310-320 nm. In an embodiment, an increase in nitric acid ion may be determined and monitored by taking repetitive measurements at approximately 220 nm.

In an embodiment, one or more fiber optic probe(s) may be inserted through the annular wall of the conversion reactor, such that the probe can detect changes in the ascorbic acid, dehydroascorbic acid, nitric acid, or combinations thereof, at a location along the length of the packed reactor. A measurement of the ascorbic acid, dehydroascorbic acid, nitric acid, or combinations thereof would be indicative of the amount of consumable reactant activity remaining for the reactor, based upon the mean-free path of gaseous $NO_2$, whereby a predetermined change in ascorbic acid, dehydroascorbic acid, nitric acid, or combinations thereof indicates that the reactor has a limited conversion capacity remaining. The value of the predetermined change can be correlated with the extent of reactor life remaining or the amount of consumable conversion media used up through suitable calibration and statistical analysis.

The combination of a fiber optic sensor probe and a spectrometer a means for monitoring the functioning of the conversion reactor and determining a lifetime of the conversion media.

In embodiments Infrared (IR) spectroscopy may be employed to detect absorbances due to particular functional groups, including but not limited to carbonyl, hydroxyl, olephinic (e.g., C.dbd.O, C.dbd.C, —OH), present on a reactant or product for ascorbic acid and dehydroascorbic acid, as would be known in the art of organic spectroscopy.

It should be understood that spectrometry may be combined as a detection method with the other metering techniques discussed herein, where for example an optical fiber may be used in conjunction with an electrochemical probe at the same sample point to gather a combination of different chemical information at the same time from the same point, or in conjunction with gas chromatograph sampling to detect for example $NO_2$ in an exiting gas stream.

In one or more embodiments, a sample of gas constituting a portion or percentage of the gas by volume may be diverted from the gas conduit or delivery conduit to a gas chromatograph that can separate and quantify the amount of each gas of interest to determine if a clinically unacceptable amount of gas is present in the system. This could mean toxic levels of $NO_2$ or insufficient levels of NO, which could be due to insufficient levels of consumable reactant activity in the reactor, channeling and/or breakthrough of $NO_2$ without conversion to NO, or other failures of the system.

In embodiments, one or more cannula sensor probe(s) may be inserted through the wall of a conversion cartridge and/or into an open volume 150 and/or gap 175, within the cartridge to obtain samples of the gases present at the one or more sample points 210, as discussed herein. The gas sample may be communicated through a sample tube to the injector of a gas chromatograph for analysis.

The combination of a cannula sensor probe and a gas chromatograph provides a means for monitoring the functioning of the conversion reactor and determining a lifetime of the conversion media.

In embodiments, the REDOX reactions involved in converting $NO_2$ into NO by interaction with ascorbic acid and water on a silica surface can be detected by measuring changes in electrical potential generated by changes in concentration of the different chemical species of interest. For example the pH of an active surface area of consumable conversion media having ascorbic acid (I) is lower than surface area of consumable conversion media having dehydroascorbic acid (II), where dehydroascorbic is the oxidized form of ascorbic acid and is more basic. Ascorbic acid has a reduction potential of 0.127 V, and pKa's of 4.17 and 11.57, which can be measured.

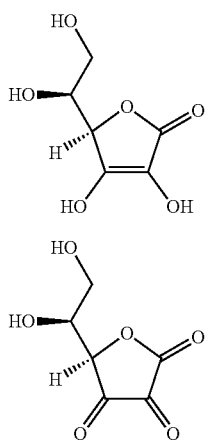

In an embodiment, a series of sensor probes, which can be micro-electrochemical sensors along the reactor's axial gas flow path, can detect changes in the oxidation/reduction potentials as ascorbic acid is converted into dehydroascorbic acid through reaction with $NO_2$. Since the oxidation potential of ascorbic acid changes with the pH, and the pH changes with ratio of ascorbic acid to dehydroascorbic acid, the relationship of concentration-to-pH-to-redox potential can be determined. When the potential measurement reaches a value indicative of predominately dehydroascorbic acid on the consumable conversion media, an electric circuit (e.g., meter) can generate a signal that can be communicated to a computer and/or produces a readout or triggers an alarm.

The combination of an electrochemical sensor probe and voltmeter and/or ammeter provides a means for monitoring the functioning of the conversion reactor and determining a lifetime of the conversion media.

In an embodiment, the reduction potential for NO of about −0.8V can be detected by one or more micro-electrochemical sensors along the reactor's axial gas flow path.

In an embodiment, the voltammetric behavior of ascorbic acid and/or dehydroascorbic acid at a glassy carbon electrode may be measured when subjected to ultrasound. Ultrasonically formed radicals may be detected due to changes in an anodic signal during a sweep voltammogram, as disclosed in Electroanalysis, Vol. 8, Iss. 3, pages 218-222, March 1996, incorporated herein by reference in its entirety.

In an embodiment, the sensor probes can be micro pH sensors that can detect changes in pH due to the conversion of ascorbic acid to dehydroascorbic acid. Micro pH sensors can have a 1 mm or sub-1 mm detection tip that can be inserted through a suitable opening in the annular wall of the conversion reactor configured and dimensioned to receive the pH sensor. The sensor can be electrically connected to an electric circuit (e.g., pH meter) that detects changes in pH, as is known in the art, and may communicate an electric signal to a computer for display and/or triggering an alarm.

The combination of a pH sensor probe and pH meter provides a means for monitoring the functioning of the conversion reactor and determining a lifetime of the conversion media.

In an embodiment, the sensor probes may be micro-conductivity sensors that can detect changes in the conductivity of the media surface due to reduced amount of water on the surface and/or differences in conductivity between the ascorbic acid and dehydroascorbic acid on the surface.

The combination of a conductivity sensor probe and voltmeter and/or ammeter provides a means for monitoring the functioning of the conversion reactor and determining a lifetime of the conversion media.

In an embodiment, the sensor probes may be magnetic probes sensors that can detect changes in the conductivity of the media surface due to reduced amount of water on the surface and/or differences in conductivity between the ascorbic acid and dehydroascorbic acid on the surface.

The combination of a magnetic sensor probe and voltmeter and/or ammeter provides a means for monitoring the functioning of the conversion reactor and determining a lifetime of the conversion media.

In embodiments, a plurality of sensors can be arrayed both axially and circumferentially, so that multiple rows of sensors are arranged 180.degree., 120.degree., 90.degree., or 45.degree. apart and sensors in each row are separated by a uniform distance along the length of the consumable conversion media, as depicted in FIGS. 5, 9, and 10. The evenly spaced axial and circumferential sensors can detect a depletion front propagating from the inlet, where $NO_2$ enters the reactor, to the outlet, where NO should exit the reactor, as each circumferential ring of sensors detects the conversion of the ascorbic acid to dehydroascorbic acid. The axial and circumferential sensors may also detect channeling through the consumable conversion media, as particular axial sensors detect conversion and deactivation of the media before other sensors around the same circumferential ring. For example, a particular axial row of sensors may detect pH values or reduction potential values indicating depletion of the ascorbic acid along a particular axial path of the reactor before other rows of sensors detect equivalent values, thereby indicating axial channeling of the $NO_2$ flow along a side of the reactor.

In an embodiment, the sensor(s) can be embedded into the consumable conversion media of the packed reactor along the reaction path, thereby providing an electrochemical map of the reaction zone.

In an embodiment, voltages and/or currents can be detected using suitable electronics, as would be known to those of ordinary skill in the art, and an electronic signal may be sent to a computer to generate a readout, a visual depiction of the sensor array and readings, and/or trigger an alarm if depletion or breakthrough is imminent. Reactor depletion may be determined by a majority of circumferential sensors located approximately equal distant from the reactor outlet showing consumable reactant inactivity, whereas break through may be determined by an axial string of sensors including at least one closest to the outlet showing consumable reactant inactivity.

Principles and embodiments of the present invention relate to a method of detecting channeling of gas flow through a packed conversion reactor by detecting pH values and/or redox potentials at a plurality of pH and/or redox sensors arranged in an annular array around the periphery of a cylindrical volume of consumable conversion media.

In an embodiment of the present invention, an array of pH and/or redox sensors can determine when a gas of interest will break through to the outlet of a conversion reactor by detecting a threshold value for at least one sensor located closest axially to the outlet.

As each sensor in an array indicates consumable reactant inactivity due to conversion to dehydroascorbic acid, it would indicate that a particular volume of consumable conversion media surrounding the sensor has been depleted or compromised.

In an embodiment of the present invention, a meter may be placed at the distal end of the conversion reactor outlet to detect one or more gasses of interest exiting the reactor, in particular, an $NO_2$ sensor probe may be located in the delivery conduit connected to the outlet to measure the amount of $NO_2$ leaving the conversion reactor. The sensor probe may be a chemical or electrochemical sensor that reacts with the exiting $NO_2$ and converts it to another chemical species, thereby removing the detected amount of $NO_2$ from the delivery gas stream flowing to a recipient.

Principles and embodiments of the present invention also relate to detecting conversion media components of interest by electrogenerated chemiluminescence (ECL), for example by detecting the emission of photons at one or more electrochemical sensor probes with an optical fibbed probe and spectrometer.

In exemplary embodiments, sensor information above can be quantified to determine the remaining useful life of a $NO_2$-to-NO reactor cartridge and/or a break-through of $NO_2$, and/or provide an indication of the remaining useful life and/or break-through. For example, information from a plurality of sensors at discrete locations in the reactor cartridge can be considered to be indicative of the remaining useful life at the sensor's discrete location, and may be mapped. Information from discrete locations can be quantified to indicate the remaining useful life of the reactor cartridge as a whole.

Principles and embodiments of the present invention relate to determining the mass and/or volumetric amount of $NO_2$ that can be converted to NO by a conversion reactor, applying a safety margin to the determined volume of $NO_2$, and recording the determined value for later reference. In an embodiment, the safety factor is applied to compensate for statistical variations in manufacturing, tolerances, and performance characteristics of the reactor, as well as real-world inaccuracies in measurements. The determined value and safety factor establishes a theoretical $NO_2$ break-through value at which the reactor would be considered depleted and requiring replacement to maintain safe operation.

In embodiments, the amount of $NO_2$ passing into a characterized reactor can be measured by an appropriate mass flow meter(s), for example a vane flow meter, a hot wire flow meter, a membrane temperature sensor, or a Karman Vortex meter. Once the amount of $NO_2$ measured by the flow meter reaches the determined value of the reactor, flow of the $NO_2$ can be halted to prevent break-through to a recipient. In embodiments, a flow meter can be placed between the gas source and the conversion reactor. A valve can be placed downstream of the flow meter and before the conversion reactor. When the amount of gas passing through the flow meter reaches the theoretical $NO_2$ break-through value, a computer can trigger the valve downstream of the flow meter to close, thereby shutting off gas flow to the reactor and halting the delivery of $NO/NO_2$ to a recipient. In embodiments, an auxiliary air/$O_2$ line can be provided in parallel to the conversion reactor line, so that air/$O_2$ may continue to flow to the recipient after the $NO_2$ gas source is valved off.

The flow meter and voltmeter and/or ammeter provides a means for monitoring the functioning of the conversion reactor and determining a lifetime of the conversion media.

Figure 14:
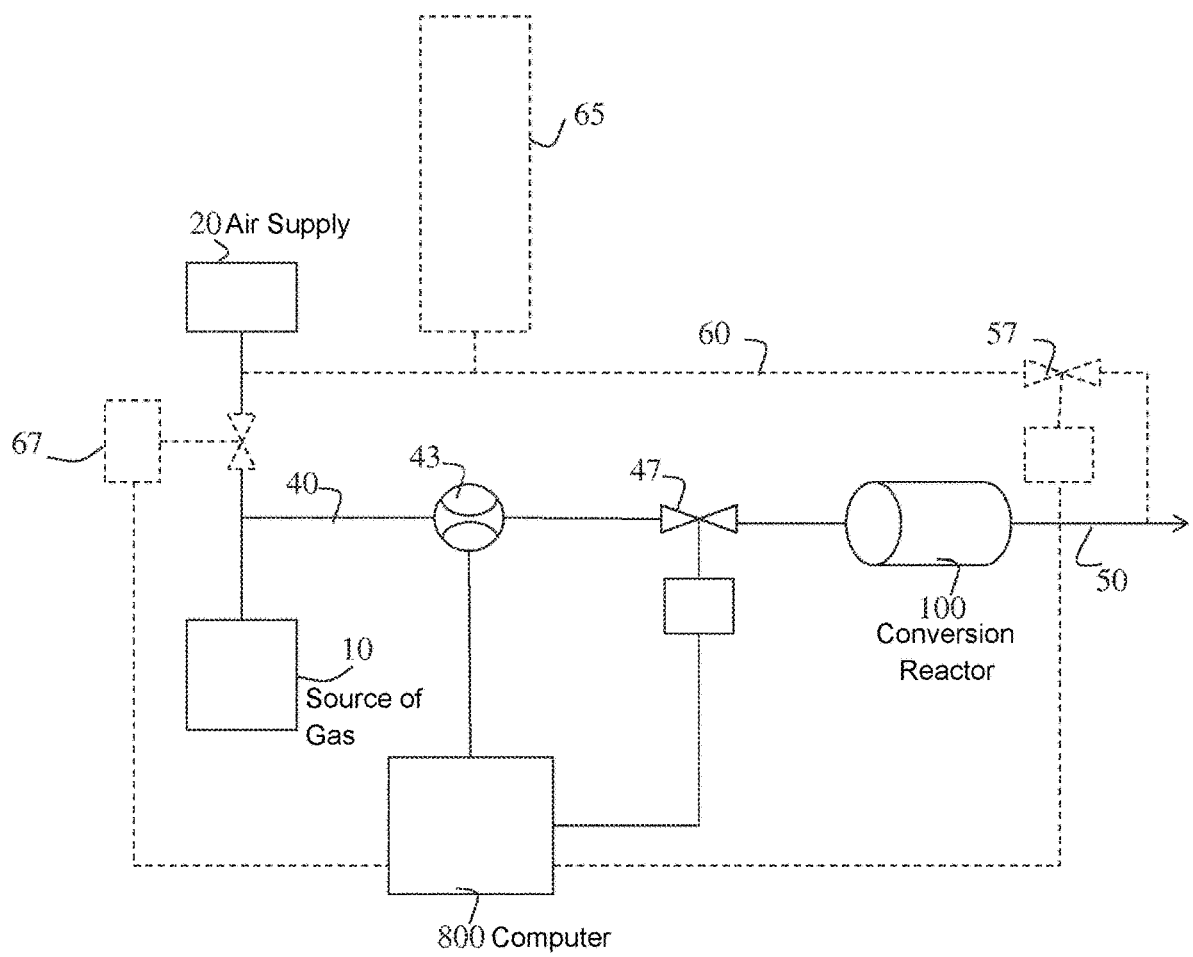
FIG. 14 illustrates an exemplary inhalation therapy system with computer controlled gas delivery, in accordance with exemplary embodiments of the present invention.

FIG. 14 illustrates an inhalation therapy system 1 having a gas source 10 that can supply for example $NO_2$ through a source conduit 40 to a flow meter 43. Gas exiting the flow meter can be fluidly communicated to a valve 47 and from the valve 47 to a conversion reactor 100 by the source conduit 40. Gas entering the conversion reactor 100 may be converted to a product gas, for example NO, and fluidly communicated from the reactor to a recipient through a delivery conduit 50. A computer 800 in electrical communication with the flow meter 43 monitors the amount of gas passing through the meter and can calculate the amount of $NO_2$ fed to the conversion reactor based on its concentration in the gas source 10. When the computer 800 determines that the amount of $NO_2$ fed to the conversion reactor has reached a predetermined value established for the reactors expected life, the computer can send an electrical signal to the valve 47 triggering it to close in order to prevent toxic $NO_2$ from flowing through an exhausted conversion reactor 100 and reaching the recipient.

In an embodiment, a valve 57 may be connected to and in fluid communication with the delivery conduit 50 and an air supply 20, and a valve 67 may be located between the air supply 20 and gas source 10. When the computer 800 determines that the amount of $NO_2$ fed to the conversion reactor has reached a predetermined value established for the reactors expected life, the computer 800 can send an electrical signal to valve 57 to open at the same time that valve 47 is triggered to close, in order to continue providing air to the recipient through the delivery conduit without any $NO_2$ or product gases. A valve 67 may be triggered to close by the computer 800 to isolate the air supply 20 from the source gas 10, so only air is provide through alternate conduit 60.

In another embodiment, a gas source 65 supplying NO may be connected to and in fluid communication with the air supply 20 and alternate conduit 60 to provide a predetermined concentration of NO to the recipient when valve 47 closes.

The determined value for the characterized conversion reactor can be stored in a suitable non-volatile memory device or other non-transitory computer readable media (e.g., 1- or 2-D bar codes) provided with or attached to the characterized reactor, or stored in the non-volatile memory of a microprocessor-based system. In an embodiment, the flow meter may be in electronic communication with the microprocessor-based system, and communicate real time measured values from a flow meter to the microprocessor-based system for determination of the remaining life of the reactor and the occurrence of a theoretical break-though. The break-through is referred to as theoretical because it is based upon the calculated value including the safety factor, so the threshold value should be reached before any actual break-through of $NO_2$ occurs.

Characterization of reactors can be accomplished by testing a statistical sampling of each manufactured batch of reactors to failure, averaging the volume of $NO_2$ converted to NO before reaching a break-through limit or consumable reactant exhaustion, and applying a suitable safety factor to adjust for both the statistical dispersion and/or variation of the measurements and variability in component and manufacturing tolerances, as well as an applicable additional safety margin to allow for example time to reach a reactor and perform the necessary replacement before actual breakthrough would occur.

Principles and embodiments of the present invention also relate to a method of determining the consumable reactant exhaustion of a conversion reactor comprising measuring an amount of reactant gas that can be converted into a product gas by a predetermined amount of consumable reactant material, determining the amount of consumable reactant material in a conversion reactor, monitoring the amount of reactant gas flowing into the conversion reactor over time with a flow meter, communicating the amount of gas to a computer configured to record and display the amount of gas that has entered the conversion reactor, and triggering an alarm when the amount of gas that has entered the conversion reactor equals or exceeds the amount of reactant gas that can be converted into a product gas by amount of consumable reactant material in a conversion reactor.

Principles and embodiments of the present invention also relate to a method of halting the flow of toxic gases to a recipient in response to the presence of toxic gas components by detecting either the presences of toxic gas entering the delivery conduit or a failure of a conversion reactor to properly function, or both, by one or more sensor(s), communicating a signal from the one or more sensor(s) to a computer indicating reactor failure or toxic gas presence, communicating a signal to a gas regulating device, and halting the flow of toxic gas to the delivery conduit by communicating a signal to the gas regulating device that changes the device from flow configuration to a no-flow configuration.

Figure 15:
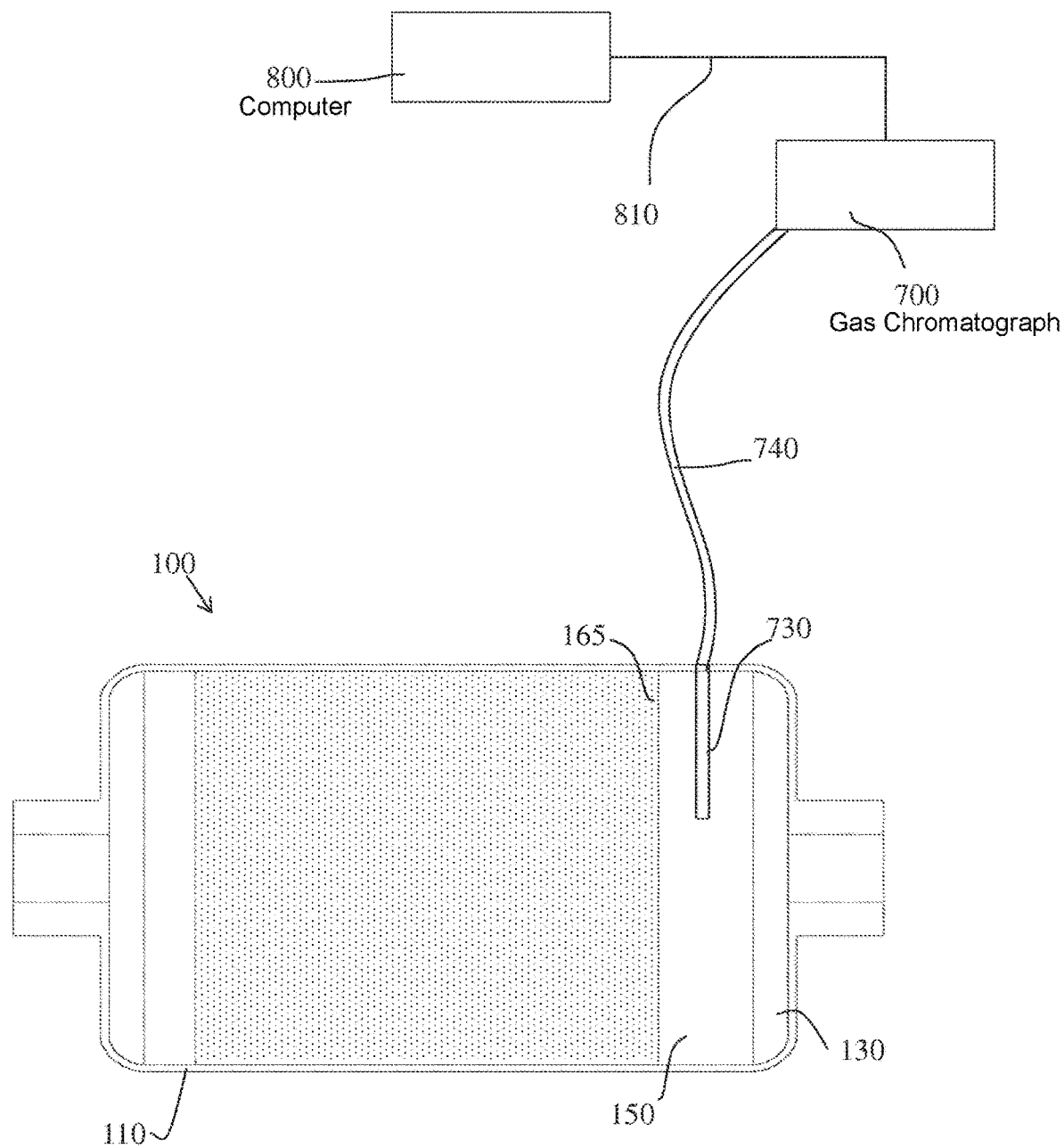
FIG. 15 illustrates an exemplary $NO_2$—NO reactor cartridge with a gas chromatograph sensor probe, in accordance with exemplary embodiments of the present invention.

In a non-limiting example illustrated in FIG. 15, a sample probe 730, which may be a cannula, can be positioned in the internal volume 150 at the outlet end of the reactor 100. The sample probe 740 may be located in the exiting gas flow, so that exiting gas components may enter the sample probe and be conveyed to a meter, for example a gas chromatograph, for qualitative and/or quantitative analysis. When $NO_2$ passes through the conversion media unreacted, the $NO_2$ reaches the outlet end of the reactor and at least a portion of the exiting gas is sampled by the sample probe and measured by the gas chromatograph indicating $NO_2$ is leaving the cartridge. The cannula sensor probe 730 can be inserted into the reactor 100 through an opening in the annular wall 110 of the body, and configured to receive at least a portion of the gas within the cartridge. The cannula can be connected to an in fluid communication with a meter (e.g., gas chromatograph) for measurement of the gas components of interest. The gas transport line 740 can receive samples of the gas entering sample probe 730, for example under pressure, and communicate the gas to a gas chromatograph 700 for component detection and concentration measurement, for example peak height and retention time, as would be known in the art of chromatographic analysis. Detection of a characteristic detection peak to indicate the presence of particular gas components (e.g., $NO_2$) could be communicated over a communication path 790 to a computer 800 for display, triggering an alarm, or both. In an embodiment, the sample probe 730, gas chromatograph 700, and computer 800 may be configured to detect a concentration of 0.1 ppm $NO_2$ or greater in the gas stream exiting the conversion reactor, or a concentration of 1.0 ppm $NO_2$ or greater in the gas stream.

It is to be understood that the invention is not limited to the details of construction or process steps set forth in the above description. The invention is capable of other embodiments and of being practiced or being carried out in various ways.

Various exemplary embodiments of the invention are described in more detail with reference to the figures. It should be understood that these drawings only illustrate some of the embodiments, and do not represent the full scope of the present invention for which reference should be made to the accompanying claims.

Various exemplary embodiments of the invention can be used to deliver therapeutic gas to patients suffering from chronic obstructive pulmonary disease (COPD), idiopathic pulmonary fibrosis (IPF), and pulmonary hypertension (PH), cystic fibrosis (CF), to name a few. At times, the name of a specific disease may not be provided; however, this is merely for ease.

Although the invention herein has been described with reference to particular embodiments, it is to be understood that these embodiments are merely illustrative of the principles and applications of the present invention. It will be apparent to those skilled in the art that various modifications and variations can be made to the devices, systems, and methods of the present invention without departing from the spirit and scope of the invention. Thus, it is intended that the present invention include modifications and variations that are within the scope of the appended claims and their equivalents.

Reference throughout this specification to "one embodiment," "certain embodiments," "one or more embodiments" or "an embodiment" means that a particular feature, structure, material, or characteristic described in connection with the embodiment is included in at least one embodiment of the invention. Thus, the appearances of the phrases such as "in one or more embodiments," "in certain embodiments," "in one embodiment" or "in an embodiment" in various places throughout this specification are not necessarily referring to the same embodiment of the invention. Furthermore, the particular features, structures, materials, or characteristics may be combined in any suitable manner in one or more embodiments.

What is claimed is:

1. A system for safely delivering a supply of nitric oxide (NO) to a recipient, comprising:
   a gas source that supplies a gas, wherein the gas supplied by the gas source is nitrogen dioxide ($NO_2$);
   a gas conduit connected to and in fluid communication with the gas source;
   a $NO_2$-to-NO reactor cartridge connected to and in fluid communication with the gas conduit, so as to allow gas to flow from the gas source to an inlet end of the $NO_2$-to-NO reactor cartridge, wherein the $NO_2$-to-NO reactor cartridge further comprising an outlet end and an internal volume comprising a consumable conversion media;
   one or more sensor probe(s) is configured to be inserted through an opening of a wall of the $NO_2$-to-NO reactor cartridge and into the internal volume of the $NO_2$-to-NO reactor cartridge and is configured to monitor the functioning of the $NO_2$-to-NO reactor cartridge operatively associated with the $NO_2$-to-NO reactor cartridge, wherein the one or more sensor probe(s) are selected from a group consisting of one or more cannula sensor probe(s) and one or more fiber optic sensor probe(s);
   a delivery conduit connected to and in fluid communication with an outlet end of the $NO_2$-to-NO reactor cartridge, wherein the delivery conduit is operable to allow NO gas from the $NO_2$-to-NO reactor cartridge to flow to the recipient;

a computer in electronic communication with the one or more sensor probe(s) over a communication path, wherein the computer is configured to receive electronic signals from the one or more sensor probe(s) and calculate a performance value; and a regulating means in electronic communication with the computer over a communication path; wherein the regulatory means is controlled based on the performance value.

2. The system of claim 1, wherein the gas sample is communicated through a sample tube to an injector of a gas chromatograph for analysis.

3. The system of claim 2, wherein the one or more cannula sensor probe(s) and gas chromatograph monitor the functioning of the conversion reactor and determine a lifetime of the conversion media.

4. The system of claim 1, wherein the internal volume further comprises a coated porous material at the outlet end of the reactor and the one or more fiber optic sensor probe(s) are operable to receive a signal from at least one surface of the coated porous material.

5. The system of claim 4, wherein the coated porous material comprises a color-active agent.

6. The system of claim 5, wherein the one or more fiber optic sensor probe(s) supplies a radiant source, and the one or more fiber optic sensor probe(s) receives light reflected off of the color-active agent and communicates the light to a spectrometer for wavelength detection and intensity measurement.

7. The system of claim 1, further comprising a flow meter for measuring an amount of gas entering the $NO_2$-to-NO reactor cartridge.

8. The system of claim 1, further comprising a flow meter for measuring an amount of gas being delivered to the recipient.

9. The system of claim 1, further comprising an $NO_2$ sensor operationally associated with the delivery conduit configured to determine a presence of an unacceptable level of $NO_2$ in the gas being directed to the recipient.

10. The system of claim 1, wherein the performance value is calculated and utilized for comparison with a predetermined threshold value, the computer is configured to generate an actuating signal when the performance value falls below the threshold value, and the regulating means is configured to receive the actuating signal from the computer, wherein the regulating means is configured to halt the delivery of the gas to a recipient when the actuating signal is received from the computer.

11. The system of claim 10, wherein the threshold value indicates that a predetermined amount of the consumable conversion media has been reached, and wherein the computer is configured to alert a user through a display, an audible alarm, or both that the $NO_2$-to-NO reactor cartridge is exhausted or compromised.

12. A method of monitoring the performance of a nitrogen dioxide ($NO_2$)-to-nitric oxide (NO) reactor cartridge, the method comprising:

incorporating one or more sensor probe(s) into an $NO_2$-to-NO reactor cartridge comprising a conversion media in an internal volume, wherein the one or more sensor probe(s) are operatively associated with the $NO_2$-to-NO reactor cartridge, wherein the one or more probe(s) is configured to be inserted through an opening of a wall of the $NO_2$-to-NO reactor cartridge and into the internal volume of the $NO_2$-to-NO reactor cartridge and the one or more sensor probe(s) are selected from a group consisting of one or more cannula sensor probe(s) and one or more fiber optic sensor probe(s); and operatively associating at least one meter with the one or more sensor probe(s) and wherein the one or more sensor probe(s) are embedded into the conversion media;

calculating a performance value based on electronic signals from the one or more sensor probe(s); and controlling a regulating means based on the performance value.

13. The method of claim 12, further comprising obtaining samples of gases present at one or more sample points in the $NO_2$-to-NO reactor cartridge from the one or more cannula sensor probe(s).

14. The method of claim 13, further comprising:
communicating a gas sample of the gas samples through a sample tube to an injector of a gas chromatograph for analysis;
monitoring the functioning of the conversion reactor with a computer; and
determining a lifetime of the conversion media.

15. The method of claim 12, wherein the internal volume of the $NO_2$-to-NO reactor cartridge further comprises a coated porous material at an outlet end of the reactor and the one or more fiber optic sensor probe(s) are operable to receive a signal from at least one surface of the coated porous material.

16. The method of claim 15, wherein the coated porous material comprises a color-active agent.

17. The method of claim 16, further comprising:
supplying a radiant source from the one or more fiber optic sensor probe(s) supplies;
receiving light reflected off of the color-active agent in the one or more fiber optic sensor probe(s); and
communicating the light to a spectrometer for wavelength detection and intensity measurement.

* * * * *